United States Patent
Buhr et al.

(10) Patent No.: US 6,395,305 B1
(45) Date of Patent: May 28, 2002

(54) REDUCTION OF SPERM SENSITIVITY TO CHILLING

(75) Inventors: Mary Buhr; Liwei He, both of Guelph (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 09/509,139

(22) PCT Filed: Sep. 22, 1998

(86) PCT No.: PCT/CA98/00892

§ 371 (c)(1),
(2), (4) Date: Jun. 30, 2000

(87) PCT Pub. No.: WO99/15010

PCT Pub. Date: Apr. 1, 1999

Related U.S. Application Data

(60) Provisional application No. 60/059,462, filed on Sep. 22, 1997.

(51) Int. Cl.[7] .................. A61K 9/127; A61K 35/24; A61K 31/685; A01N 1/100; A01N 1/02
(52) U.S. Cl. .................. 424/520; 424/450; 424/537; 435/1.3; 435/2; 514/78
(58) Field of Search .................. 424/520, 537, 424/450; 435/2, 1.3; 514/78

(56) References Cited

U.S. PATENT DOCUMENTS

| | | | |
|---|---|---|---|
| 4,356,259 A | | 10/1982 | Banba |
| 4,677,099 A | * | 6/1987 | Shinitzky et al. |
| 4,921,706 A | * | 5/1990 | Roberts et al. |
| 4,965,186 A | | 10/1990 | Grischenko et al. |
| 5,595,982 A | * | 1/1997 | Harless |
| 5,665,380 A | * | 9/1997 | Wallach et al. |
| 5,759,764 A | | 6/1998 | Polovina |
| 5,895,749 A | * | 4/1999 | Alvarez |

OTHER PUBLICATIONS

Faraq et al., Fette, Seifen, Anstrichmittel, 84(8): 313–17. Cold shock and various extender effects on physical and chemical characteristics of ram sperms, 1982.*
Foote et al., Reprod. Fertil. Dev., 5: 665–73. Factors affecting preservation and fertility of bull sperm: a brief review, 1993.*
Milovanov et al., Dokl. Vses. Akad. S–kh. Nauk im. V. I. Lenina, 11: 25–6. Cryoprotectant effect of egg yolk lipoproteins on the survival of sperm of livestock, 1985.*
Buhr, M..M. et al., Lipids in Extenders Affect Boar Sperm Function During Cryopreservation, Boar Sperm Preservation IV Proceedings IV International Conference on Boar Semen Preservation, Beltsville, MD, Aug. 1999.
Liwei He, Incorporating Lipids into Boar Sperm Reduces Their Sensitivity to Chilling and Cryopreservation, Sep. 1997.
Document from presentation at 30th Annual Meeting of the Society for the Study of Reproduction, Portland, OR, Aug. 2–5, 1997.
Blumenthal, R. et al., "Liposomelymphocyte interaction: saturable sites for transfer and intracellular release of liposome contents", *Proc.Natl. Acad.Sci. USA*, vol. 74, 5603–5607 (1977).
Buhr, M. et al., "Effects of semen preservation on boar spermatozoa head membranes", *Gamete Res.*, vol. 23, 441–449 (1989).
Bwanga, C. et al., "Cryopreservation of boar semen I: A literature review", *Acta Vet. Scand.*, vol. 32, 431–453 (1991).
Darin–Bennett, A. et al., "The effect of cold shock and freeze–thawing on release of phospholipids by ram, bull and boar spermatozoa", *Aust.J.Biol.Sci.*, vol. 26, 1409–1420 (1973).
Darin–Bennett, A. et al. "The phospholipids and phospholipid–bound fatty acids and aldehydes of dog and fowl spermatozoa", *J. Reprod.Fert.*, vol. 41, 471–474 (1974).
Darin–Bennett, A. et al., "Influence of the cholesterol content of mammalian spermatozoa on susceptibility to cold–shock", *Cryobiol.*, vol. 14, 466–470 (1977).
Deamer, D. et al., "Relation of liposomes to cell membranes" *Structure and Properties of Cell Membranes.* 1985, vol. III, 104–119. Ed. Gheorghe Benga, CRC Press, Inc., Boca Raton, Florida.
Flechon, J.E. et al., "Membrane fusion events in the Ca++/ionophore–induced acrosome reaction of ram spermatozoa", *J. Cell. Sci.*, vol. 81, 43–63 (1986).

(List continued on next page.)

*Primary Examiner*—Christopher R. Tate
*Assistant Examiner*—Michele C. Flood
(74) *Attorney, Agent, or Firm*—Synnestvedt & Lechner LLP

(57) ABSTRACT

Cryopreserved boar spermatozoa is much less fertile than that of other species, which could be due to damage to sperm membrane lipids during the cryopreservation process. Incorporation of selected lipids improves the survival of boar spermatozoa following cryopreservation.

Liposomes were made from lipids extracted from head plasma membrane (HPM) of boar spematozoa or from selected lipids (SL) which contained specific phospholipids. At a fixed lipid concentration, fusion efficiency with spermatozoa as measured by flow cytometry and R18 dequenching was affected by lipid type, sperm concentration and incubation time.

SL and HPM improved sperm viability (SYBR-14 and propidium iodide) and motility during cooling to 5C., with SL±egg yolk better than or equal to HPM (P<0.05). Post-thaw, egg yolk showed a strong cryoprotective effect. Compared to HPM, SL-treated sperm had higher post-thaw viability, progressive motility and total motility in the extender including egg yolk and higher viability in the extender excluding egg yolk (P<0.05).

25 Claims, 7 Drawing Sheets

OTHER PUBLICATIONS

Foulkes, J.K., "Separation of lipoproteins from egg yolk and their effects on the motility and integrity of bovine spermatozoa", *J. Reprod. Fert.*, vol. 49, 277–284 (1977).

Gebauer, M.R. et al., "Mobility of bovine spermatozoa extended in "defined" diluents", *J. Dairy Sci.*, vol. 53, 817–823 (1970).

He et al., "Membrane–incorporated lipids affect chilling sensitivity of boar semen", *Biol Reprod.*, 56S1, 97 (1997).

Hofmo, P.O. et al., "Recent developments in freezing of boar semen with special emphasis on cryoprotectants" Boar Semen Preservation II. Proc. $2^{nd}$. Int. Conf. Boar Semen Preserv. Beltsville. Suppl. 1. Reprod. Domestic. Anim. 1991, vol. (s1) 111–122. Eds. L.A.Johnson and D.Rath. Paul Parey Scientific Publishers, Berlin and Hamburg.

Holt, W.V. et al., "Determination of lipid composition and thermal phase transition temperature in an enriched plasma membrane fraction from ram spermatozoa", *J. Reprod. Fert.*, vol. 73, 285–294 (1985).

Huang, C.H. "Studies on phosphatidylcholine vesicles: Formation and physical characteristics", *Biochemistry*, vol. 8, 344–352 (1969).

Huang, L. "Liposome–cell interactions in vitro" *Liposomes* 1983, 87–124. Ed. Marc J. Ostro, Marcel Dekker, Inc. New York and Basel.

Jones, M.N. et al., "The liposomal state" *Micelles, Monolayers, and Biomembranes* 1995, 117–142. Eds. Malcolm N Jones and Dennis Chapman. A John Wiley & Sones, Inc.

Paquignon, M. "Freezing and thawing extenders for boar spermatozoa" Deep Freezing of Boar Semen. Proc. $1^{st}$ Int. Con. Deep Freeze. Boar Semen. Uppsala. P. 1985, 129–145. Eds. L.A. Johnson and K. Larsson. Swedish University of Agricultural Sciences, Uppsala.

Poulos, A. et.al., "The phospholipid–bound fatty acids and aldehydes of mammalian spermatozoa", *Comp. Biochem. Physiol.*, 46B, 541–549 (1973).

Pringle, M. et al., "Biomembrane structure and effects of temperature" Effects of low temperatures on biological membranes 1981, 21–37. Eds. G.J. Morris and A. G. Clarke. Academic Press, London.

Pursel, V.G. et al., "Interaction of extender composition and incubation period on cold shock susceptibility of boar spermatozoa", *J.Anim.Sci.*, vol. 35, 580–584 (1972).

Pursel, V.G. et al., "Effect of dilution, seminal plasma and incubation period on cold shock susceptibility of boar spermatozoa", *J. Anim. Sci.*, vol. 37, 528–531 (1973).

Robertson, L. et al., "Effects of cold shock and phospholipase A2 on intact boar spermatozoa and sperm head plasma membrane", *Mol. Reprod. Dev.*, vol. 26, 143–149 (1990).

Streiner, C.F. et al., "The mechanism of phosphatidylserine liposome interaction with sperm for cryopreservation", *Biol Reprod*, 48S1, Abst 423 (1993).

Watson, P.F., "The interaction of egg yolk and ram spermatozoa studies with fluorescent probe", *J. Reprod. Fert*vol., 42, 105–112 (1975).

Watson, P.F., "The effects of cold shock on sperm cell membranes" Effects of low temperatures on biological membranes 1981, 189–218. Eds. G.J. Morris and A. Clarke. Academic Press, London.

Watson, P.F. et al., "Cold shock injury in animal cell" Temperature and Animal Cells. Eds. K. Bowler and B.J. Fuller Symp. Soc. Exp. Biol. 1981, vol. 41: 311–340.

Watson, P.F. et al., "The responses of boar sperm membranes to cold shock and cooling" Deep Freezing of Boar Semen. Proc. $1^{st}$. Int. Con. Deep Freeze. Boar Semen. Uppsala. 1985, 113–127. Eds. L. A. Johnson and K. Larsson. Swedish University of Agricultural Sciences, Uppsala.

Wilhelm, K. M. et al., "Effects of phosphatidylserine and cholesterol liposomes on the viability, motility and acrosomal integrity of stallion spermatozoa prior to and after cryopreservation", *Cryobiology*, vol. 33, 320–329 (1996).

* cited by examiner

| Time (min) | Temp. (C) | Contents | Viability |
|---|---|---|---|
| −20 | 34 | BTS ± HPM or SL | |
| 0 | 34 | Sperm + BTS ± HPM or SL | 34C, t=0 |
| 60 | 0.1C/min ↓   4.6–5.6C/min → 0–5C  Cold Shock | | 0–5C. t=60 |
| 100 | 24 | | 24 C, t=100 |
| 110 | 24 | | |
| | 0.1C/min ↓ | | |
| 300 min. | 5 | | 5C, t=300 |

FIG. 1

REDUCTION OF SPERM SENSITIVITY TO CHILLING

CROSS REFERENCE TO RELATED APPLICATIONS

This application is a U.S. national stage application based on International Application No. PCT/CA98/00892, filed Sep. 22, 1998, which is a continuation-in-part of U.S. Provisional Application No. 60/059,462, filed Sep. 22, 1997, now abandoned.

BACKGROUND OF THE INVENTION

The present invention relates to a method of preserving sperm to be used for the artificial insemination of domestic animals, and especially for the artificial insemination of swine and bovine. The invention can also find application in avian, other domestic animals and human sperm.

THE PRIOR ART

The most common method of sperm preservation is cryopreservation. During the process of cryopreservation, freezing and thawing damage cell membranes. Mammalian sperm are sensitive to rapid cooling. This phenomenon, called cold shock, occurs when the environmental temperature of sperm rapidly decreases from 35–37° C. (body temperature) down to a few degrees above zero (Watson and Plummer, 1985). For boar sperm, even slow cooling below a temperature of +15° C. results in a decreased survival rate (Watson and Plummer, 1985). Cryopreserved boar semen is used on a very small scale for artificial insemination because of reduced fertility compared to fresh sperm (Johnson and Larson, 1985; Hofmo and Almlid, 1991; Bwanga, 1991). Many experiments (reviewed by Watson and Plummer, 1985) attribute this poor performance to the detrimental effect of cryopreservation on the sperm membrane.

Sperm injury is manifested as loss of selective permeability and loss of integrity of the plasma membrane, outer acrosomal membrane, and mitochondria (reviewed by Parks and Lynch, 1992). These manifestations are accompanied by loss of motility, decreased energy production, changes to membrane lipid composition (Parks and Lynch, 1992; Buhr et al., 1994) and changes to membrane dynamic behaviour (Buhr et al., 1989; 1994). In order to use sperm for artificial insemination, there is a need to prevent and repair loss of selective permeability and loss of integrity of the plasma membrane, outer acrosomal membrane, and mitochondria. There is a need to characterize the damage to sperm during cryopreservation. There is also a need to develop compositions and methods that may be used to prevent and repair the damage to sperm during cryopreservation so that survival of sperm may be increased.

Susceptibility of sperm to cryopreservation differs across species and with stage of spermatozoal maturation. It could be partially due to the different lipid composition of sperm membranes as evidenced by: 1. Sperm from different animal species with similar cold shock resistance, have rather similar lipid composition, length and saturation of fatty acid chains (Watson and Plummer, 1985; Parks and Lynch, 1992); 2. Sperm from different parts of the epididymis have different sensitivity to cold shock, which is correlated with the changes in lipid composition during sperm maturation from caput to cauda epididymis (Bwanga, 1991); 3. Some lipids are released from sperm membranes during cold shock (Darin-Benneett et al., 1973; Bwanga, 1991); 4. The main protective factor from egg-yolk is crude lipid which has been demonstrated to interact with sperm plasma membrane (Gebauer et al., 1970; Pursel et al., 1972; Watson, 1975; Foulkes, 1977); and 5. Addition of some lipids to the extender has been suggested to have beneficial effects on cold resistance (Paquignon, 1985). These compositions have not significantly improved boar sperm viability after cryopreservation.

The nature and amount of specific lipids in sperm membranes differ among animal species (Darrin-Bennett et al., 1974; Poulos et al., 1973; Parks and Lynch, 1992: Buhr et al., 1994), which is consistent with the species' differences in the susceptibility of sperm to cold shock (Watson and Morris, 1981; Watson and Plummer, 1985). Sperm from rooster (Parks and Lynch, 1992; Watson, 1981), human and monkey (Holt and North, 1985), rabbit and dog (reviewed by Watson and Plummer, 1985) are more resistant to cold shock than that from domestic animals, such as bull, ram, horse and boar, with boar sperm being the most sensititive (Watson, 1981). The results from Parks and Lynch (1992) showed that the ratio of sperm membrane proteins to phospholipids (wt:wt) was lowest for rooster at 0.46, intermediate for bull and stallion (0.80 and 0.86) and highest for boar (1.26). They also found that the ratio of cholesterol to phospholipid was close to 1 in human and monkey, but less than 0.8 in bull, ram and boar (Holt and North, 1985).

Using exogenous lipid as a cryoprotectant in semen cryopreservation has been tried by several groups (Butler and Roberts, 1975; Streiner and Graham, 1987; Wilhelm et al., 1996). However, a consistent improvement of post-thaw result has not been achieved, especially with boar semen. These problems could possibly be due a failure to meet a necessity for: 1. Lipids specific for different animal species. Experimental addition of phosphatidylcholine (PC), phosphatidylserine (PS) and/or cholesterol (Pursel et al., 1973; Paquignon, 1985) was based merely on the observation that egg-yolk lipoprotein has some beneficial effects on survival of cryopreservation. 2. Specific fatty acid chain length and saturation, and/or 3. Appropriate methodology to incorporate lipids into spermatozoa and monitor the incorporation efficiency.

Lipids considered common to the cell membrane such as phosphoglycerides, sphingomyelin (SPH) and cholesterol have been identified in the spermatozoa of a variety of species (Darin-Bennet et al., 1973, 1974; Darin-Bennet and White, 1977). Generally, PC is the predominant phospholipid in sperm membranes. Sphingomyelin and phosphtidylethanolamine (PE) are relatively high also. Phosphatidylserine and phosphatidylinositol (PI) are present at low levels. Lipid composition of whole sperm or isolated membranes has been shown to change during epididymal maturation in a variety of species (Nikolopoulou et al., 1985; Hall et al., 1991; Rana et al., 1991). Sperm lipids also change during capacitation and the interaction with ova (Nikolopoulou et al., 1986; Stojanoff et al., 1988; Seki et al., 1992).

Comparing sperm from domestic species, boar sperm membranes have a low percentage of PC and higher percentage of PE and SPH (De Leeuw et al., 1990), and the PI of boar is about 3 times of bull. Parks and Lynch (1992) found that bull and rooster sperm were characterized by a high ratio of PC to PE while boar and stallion sperm had a lower PC/PE ratio. Rooster sperm were also characterized by a higher percentage of phospholipid in the PS+PI fraction than other species (Parks and Lynch, 1992).

The composition of the acyl side chains of phospholipids also differs among species. Sperm membranes from cold-shock resistant species are characterized by a high degree of saturation in fatty acid chains (Darin-Bennet and White, 1977). Cold-shock susceptible species tend to have only very minor amounts of other aldehydes present, while resistant species contain large amounts of steraldehyde (18:0) and 16:1, 18:1, 18:2 aldehydes (Poulos et al., 1973; Darin-Bennett et al., 1974). Phosphatidylcholine from mammalian sperm is characterized by a very high proportion of docosapentanoyl and docosahexanoyl chains, with 22:5 predominant in boar and stallion sperm and 22:6 highest in bull sperm (Parks and Lynch, 1992). For PE, high proportion of long chain polyunsaturated fatty acyl groups, especially 22:5 and 22:6, were contained in sperm of bull, boar, stallion and ram while 22:4 was high in rooster sperm (Parks and Lynch, 1992). These results suggest that the lipid composition of sperm membranes contributes to the cold-shock sensitivity. There is a need to use information regarding the lipids and fatty acids which are damaged during cryopreservation in designing compositions for preserving semen. It would be helpful if a composition could be developed which protected and restored the specific kinds and ratio of lipids and fatty acids sperm membrane in order to improve cold resistance. There is currently no composition for improving sperm survival after cooling which is tailored to the kinds and ratio of lipids and fatty acids in sperm membrane.

Cryopreservation decreases the fertility of sperm, especially boar sperm, by reducing motility and damaging membrane integrity (Hofmo and Almlid, 1991). Changes in boar sperm membrane structure and function are manifested as dramatic alterations to both the composition and the dynamic behaviour of the lipids from sperm head plasma membranes (HPM) (Buhr et al., 1994). Modified ultrastructure was also found in boar sperm plasma membranes after cold shock (De Leeuw et al., 1990), which may affect the processes of capacitation, acrosome reaction and gamete recognition/fusion. Buhr et al. (1994) demonstrated for the first time that composition of lipids from the head plasma membrane of intact boar sperm was altered after cryopreservation. These compositional changes were correlated with significant fluidity changes in the response of the extracted lipids to temperature and calcium.

Compared to fresh sperm, cryopreserved boar sperm contained significantly less SPH and more PC (Buhr et al., 1994). The octadecanoate (18:0) content in both PC and PE decreased after cryopreservation, while the polyunsaturated fatty acids docosatetraenoate (22:4) and/or arachidonate (20:4) increased in these phospholipids and in SPH and PI. The alterations in the molecular interactions, composition, and $Ca^{++}$ sensitivity of membrane lipids may disturb the normal behaviour of membranes in the fertilization process (Buhr et al., 1994).

Cryopreservation irreversibly affects membrane mechanics, especially the lateral phase separation of membrane lipids into fluid and gel phase domains. Isolated HPM from fresh boar sperm extended in BL-1, showed a decrease in fluidity over time (Buhr et al., 1989, Robertson et al., 1990). Thus, while the decrease in fluidity over time is similar for HPMs from fresh and untreated and fresh BL1-extended semen, sperm which have been extended and cooled, frozen-thawed, or cold-shocked show different membrane fluidity patterns. As the temperature decreases, fatty acyl chains of phospholipids become rigid and phospholipids become isolated in gel domains. Membrane proteins are excluded from gel domains (Pringle and Chapman, 1981) which results in destabilization of the membrane (Flechon et al., 1986). Thus changes to membrane constituents which affect the fluidity and stability of the membrane will affect the functioning of that membrane. This harmful effect is irreversible in sperm and the techniques and extenders currently employed have not prevented this damage. Exposure then, to cold temperatures prior to cryopreservation affects the membrane's ability to regulate itself and other cellular functions, even in the presence of a cryoprotectant.

Cold-shocking sperm is also associated with the release of phospholipids from the cell membranes (Darin-Bennett et al., 1973). Although the release of total phospholipid in boar sperm was less than that seen in either bull or ram, PC and PE were preferentially released (Darin-Bennett et al., 1973). It was implied that these phospholipids were released from the acrosomal membrane, but HPM might also be involved (Bwanga, 1991). Using exogenous lipid as a cryoprotectant in semen cryopreservation has been tried by several groups (Butler and Roberts, 1975; Streiner and Graham, 1987; Wilhelm et al., 1996). However, a consistent improvement of post-thaw result has not been achieved, especially with boar semen. There is a need for a composition which increases boar sperm survival after chilling. There is a particular need for a composition which is designed to prevent and repair the damage specific to boar sperm membranes by providing lipids with specific fatty acid chain length and saturation of the lipids that are damaged by chilling of boar sperm. It would also be helpful if this composition could be used with methodology to incorporate lipids into spermatozoa and monitor the incorporation efficiency.

The invention comtemplates that liposome-cell interaction is important in sperm preservation. Phospholipids, in the presence or absence of the other amphipathic molecules such as cholesterol, typically form closed membranous vesicles when exposed to aqueous media. Small unilamellar vesicles (SUVs) are typically prepared by sonication to break up the multilamellar vesicles (MLV) (Huang, 1969). Typically, SUVs are a homogeneous population of 25 to 50 nm (Deamer and Uster, 1985, Blumenthal et al., 1977)). Theoretically, SUVs are prone to fusion, particularly at the phase transition temperature (Huang, 1983; Jones and Chapman, 1995). SUVs are more fusogenic, because they have higher surface tension due to the greater radius of curvature and because they can approach closer to the cell surface due to their small size (Huang, 1983).

Fusion efficiency can be defined generally as the occurrence of fusion or, specifically, as the extent of liposome fusion to target cells. Fusion efficiency can be determined semi-quantitatively by analysing the change of fluorescent intensity of single labelled fluorescence marker (Kok and Hoekstra, 1992) or by energy transfer between double labelled fluorescence markers (Struck et al., 1981). There are several methods for studying liposome-cell interactions (Huang, 1983), such as uptake of radioactive markers, carboxyl fluoroscein, fluorescent lipids, electron microscopy, R18 dequenching, resonance energy transfer. The method of the invention used one semi-quantitative method, either resonance energy transfer (RET) and R18 Dequenching, plus the quantitative flow cytometric technique to monitor fusion between SUVs and sperm membrane.

SUMMARY OF THE INVENTION

This invention provides compositions that incorporate specific exogenous lipids into sperm to improve their ability to survive cryopreservation. The compositions consist of lipids to be incorporated into the sperm. While other researchers have attempted to alter the molecular composition of sperm membranes, their additions have been based on assumptions about what a membrane may need in order to function better. We have taken a unique approach of: defining the particular problem—cryopreservation damages the fertilising ability of sperm by at least one mechanism not connected with sperm motility; specifying and then quantifying the specific molecules damaged in cryopreserved sperm; designing a unique mixture of phospholipids with specific fatty acid side chains; developing a method to fuse these lipids to sperm and quantitate the percentage of sperm taking up the lipids; demonstrating the enhanced resistance to chilling injury in lipid-treated sperm. These lipids were designed based on the damage we identified in cryopreserved boar sperm, which have unique membrane molecular composition, chilling sensitivity and functional parameters (calcium flux, capacitating conditions, zona penetration rate etc) when compared to all other domestic species. The same method is applied to bull sperm, which because of these differences, is not an obvious combination. The demonstrated efficacy of the lipids in bull sperm suggests that they may have universal efficacy in improving the post-thaw quality of cryopreserved sperm from many species.

The compositions also form stable SUVs under the normal physiological conditions for sperm and fuse with the sperm membranes. We also defined the incorporation conditions and fusion efficiency of selected lipids to boar and bovine sperm. An appropriate monitoring system was selected. Finally, we examined the effects of these lipids on viability and motility of boar and bovine sperm during the cooling procedure and after cryopreservation.

There is industrial utility. For example, in the bull industry, the enhanced sperm survival will mean that fewer sperm will be needed to achieve the current fertility success rates, and the industry therefore will be able to prepare more inseminating doses from the same number of sperm. In addition, bulls of high genetic merit and in strong commercial demand sometimes produce sperm which cannot survive the freezing and thawing process, and so the industry is unable to market this semen. The lipids will improve these sperm to allow meeting this established market demand. In the porcine artificial insemination industry, no current cryopreservation procedure is sufficiently efficient to allow widespread commercial use of frozen sperm. An effective freezing method will facilitate the development of a new international commercial trade in porcine genetics. Many species (domestic, exotic and endangered, including mammals and avians) have sperm that cannot survive cryopreservation, and these lipids will enable the successful preservation of this genetic material. The application of these lipids to enable successful preservation of poor quality sperm from individual males may find human medical application, and/or application in many other species.

The invention relates to a composition for increasing sperm survival, comprising a carrier, phospholipids and fatty acid chains. The invention also relates to a composition for increasing sperm survival, comprising a carrier, phospholipids and fatty acid chains, the composition being essentially absent of cholesterol. The composition can consist of phospholipids selected from the group consisting of phosphatidylcholine, phosphatidylethanolamine, sphingomyelin, phosphatidylserine and phosphatidylinositol. The composition preferably has phospholipids in a ratio where phosphatidylcholine is about 20: phosphatidylethanolamine is about 25: sphingomyelin is about 40: phosphatidylserine is about 5: phosphatidylinositol is about 5. More preferably, the composition has phospholipids in a ratio where phosphatidylcholine is about 21: phosphatidylethanolamine is about 26: sphingomyelin is about 42: phosphatidylserine is about 5: phosphatidylinositol is about 5. Most preferably, the composition has the phospholipids in a ratio where phosphatidylcholine is about 21.05: phosphatidylethanolamine is about 26.32: sphingomyelin is about 42.11: phosphatidylserine is about 5.26: phosphatidylinositol is about 5.26. In another preferred embodiment, the phospholipids are in a ratio where phosphatidylcholine is about 20: phosphatidylethanolamine is about 20: sphingomyelin is about 40: phosphatidylserine is about 10: phosphatidylinositol is about 10. Alternatively, the the phospholipids are in a ratio where phosphatidylcholine is about 25 : phosphatidylethanolamine is about 20 : sphingomyelin is about 40: phosphatidylserine is about 5 : phosphatidylinositol is about 10.

The composition preferably has the phospholipids having proportion (mol %) of:
a. phosphatidylcholine with specific fatty acid chains about:
  $C16: 0=7\%$
  $C18: 0=3\%$
  $C18: 1=5\%$
  $C18: 2=4\%$
  $C20: 4=0.8\%$
  $C22: 6=0.6\%$
b. phosphatidylethanolamine with specific fatty acid chains about:
  $C16: 0=5\%$
  $C18: 0=21\%$
c. sphingomyelin with specific fatty acid chains about:
  $C16: 0=16\%$
  $C18: 0=25\%$
  $C22: 6=5\%$
d. phosphatidylserine with specific fatty acid chains about:
  $C16: 0=0.5\%$
  $C18: 0=4\%$
  $C18: 2=0.5\%$
e. phosphatidylinositol with specific fatty acid chains about:
  $C16: 0=0.6\%$
  $C18: 0=6\%$
  $C18: 1=0.2\%$
  $C18:2=0.6\%$,
In another embodiment, the phospholipids in the composition have a proportion (mol %) of
a. phosphatidylcholine with specific fatty acid chains about:
  $C16: 0=7.37\%$
  $C18: 0=3.16\%$
  $C18: 1=5.26\%$
  $C18: 2=3.79\%$
  $C20: 4=0.84\%$
  $C22: 6=0.63\%$
b. phosphatidylethanolamine with specific fatty acid chains about:
  $C16: 0=5.26\%$
  $C18: 0=21.06\%$
c. sphingomyelin with specific fatty acid chains about:
  $C16: 0=15.97\%$
  $C18: 0=25.27\%$
  $C22: 6=5.34\%$
d. phosphatidylserine with specific fatty acid chains about:
  $C16: 0=0.53\%$ C18: 0=4.21%
C18: 2=0.53%
e. phosphatidylinositol with specific fatty acid chains about:
C16: 0=0.62%
C18: 0=6.22%
C18: 1=0.20%
C18:2=0.62%.

The phospholipids in the composition may have the phospholipids in one of the ratios described above and the fatty acid side chains in another of the ratios described above. The sperm preserved with the compositions is preferably mammalian sperm, most preferably boar sperm or bull sperm.

The compositions preferably have fatty acid chain proportions that imitate the fatty acid chain proportions found in fresh boar sperm membrane or fresh bull sperm membrane.

The compositions preferably have fatty acid chain proportions that imitate the fatty acid chain proportions found in fresh boar sperm membrane with adjustments to broaden the distribution of fatty acid chains in phosphatidyicholine. The fatty acid chain proportions may also imitate the fatty acid chain proportions found in fresh boar sperm membrane with adjustments to increase the proportion of 18:0. The fatty acid chain proportions also preferably imitate the fatty acid chain proportions found in fresh boar sperm membrane with adjustments to decrease or increase the proportion of longer unsaturated fatty acids or unsaturated fatty acids.

The fatty acid chains are preferably in about the following percentages: phosphatidylcholine 35% 16:0, 15% 18:0, 25% 18:1, 18% 18:2, 4% 20:4 and 3% 22:6. phosphatidylethanolamine 20% 16:0, 80% 18:0 and no 20:4, 22:4 and 22:6, sphingomyelin 30% 16:0, 60% 18:0, 10% 22:6 and no 20:4 or 22:4, phosphatidylserine 10% 16:0, 80% 18:0, 10% 18:2 and phosphatidylinositol 28% 16:0, 65% 18:0, 2% 18:1 and 5% 20:0.

The compositions of the invention increase sperm survival during cooling, freezing and post-thaw. The phospholipids and fatty acid chains are preferably in a vesicle, more preferably a small unilamellar vesicle (SUV). The compositions of the invention may be combined with an extender, preferably BTS, BF5, egg yolk or O.E.P. The composition of any of claims 1 to 22, wherein phospholipids and fatty acid chains are selected in proportions based on differences in membrane lipids caused by cryopreservation.

The invention also includes sperm preserved with the compositions of the invention. The invention includes a method for increasing sperm survival comprising characterizing the damage caused to sperm lipids upon cooling, freezing or thawing and administering an exogenous composition containing lipids of the type that are damaged upon cooling, freezing or thawing. In the method, the exogenous lipid composition is preferably administered in a vesicle, more preferably a small unilamelar vesicle (SUV).

The invention also includes a method for increasing sperm survival comprising administering one of the compositions of the invention.

In another embodiment, the invention includes a method of preparation of a composition for preserving sperm for in vitro or in vivo fertilization, comprising: determining and quantifying at least one of the phospholipids damaged in chilled, frozen or post-thaw sperm; preparing a composition including a carrier and at least one phospholipid with fatty acid side chains to replace at least one phospholipid damaged in chilled or frozen sperm, wherein the composition is capable of fusing to sperm to provide the sperm with resistance to chilling, freezing or post-thaw damage. The invention also includes a method of preparation of a composition for preserving sperm for in vitro or in vivo fertilization, comprising: determining and quantifying the phospholipids damaged in chilled, frozen or post-thaw sperm; preparing a composition including a carrier and phospholipids with specific fatty acid side chains to replace the phospholipids damaged in chilled or frozen sperm, wherein the composition is capable of fusing to sperm to provide the sperm with resistance to chilling, freezing or post-thaw damage. In the method, the sperm is mammalian sperm, more preferably boar sperm or bull sperm.

The invention also includes a method of performing artificial insemination in a mammal comprising administering sperm preserved with the composition of the invention to a female mammal of the same species so that the female mammal becomes impregnated with the sperm. The mammal is preferably a bovine or porcine mammal.

BRIEF DESCRIPTION OF THE DRAWINGS

FIG. 1. Cooling Procedure. Semen was pooled from two boars' ejaculates, diluted with BTS buffer (final concentration $1 \times 10^7$ sperm/ml) and incubated either with liposomes (either SL or HPM lipids; final concentration of lipids 0.3119 umole/ml) or BTS buffer as a control. Sperm were cooled as indicated. After 60 minutes (28 C.), a 500 ul sample was chilled to 0–5 C. for 5 minutes (cold shock). Viability (SYBR-14 and propidium iodide) was determined for each treatment sample at 34 (t=0 min), 0–5 C. (t=60 min, cold shock), 24 C. (t=100 min) and 5 C. (t=300 min).

*: within a sperm concentration, the % sperm with incorporated SL lipids differed from % with HPM at this incubation time ($P<0.05$). With $10^7$ sperm/ml, % sperm with with incorporated SL lipids was lowest at t=0 min ($P<0.05$); levels at 10, 30 and 60 minutes were similar.

a,b,c,d: within a sperm concentration and lipid, values with no letters in common differ ($P<0.05$)

Figure 3:
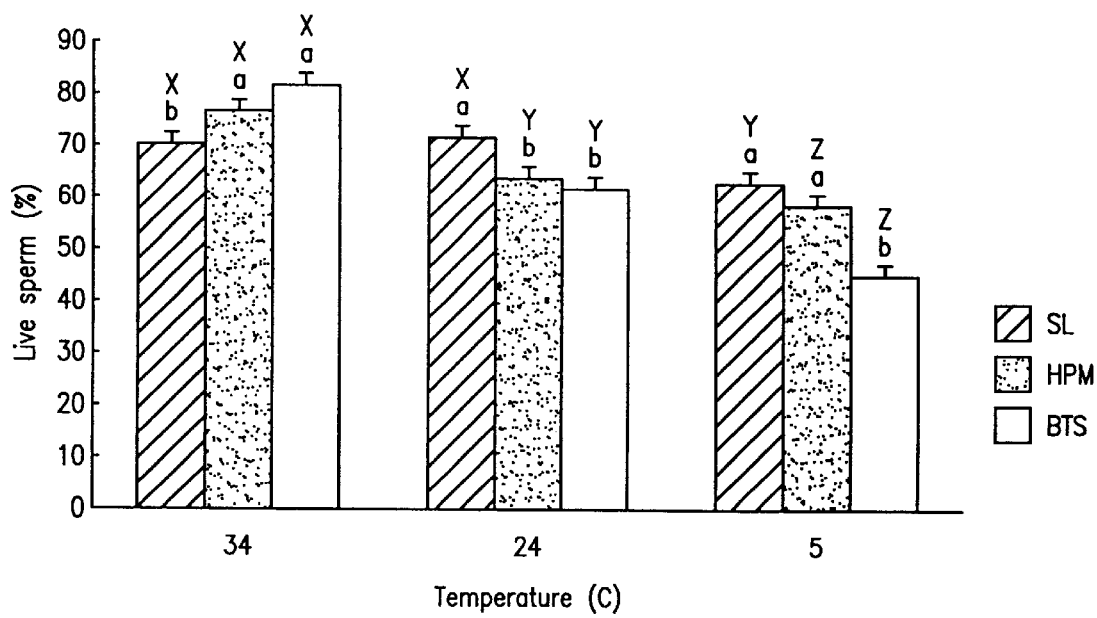

FIG. 3. Boar sperm viability during cooling process (n=3). Lipids (Select, SL; head plasma membrane, HPM, 0.3119 umole/ml) or no lipids (BTS) were added to sperm ($10^7$ sperm/ml) at 34 C. immediately after ejaculation. Sperm were cooled from 34 C. to 5 C. at 0.1 C. per minute and viability was determined with SYBR-14 and Propidium Iodide at 34 C. (immediately after treatment), 24 C. and 5 C.

a,b,c: within a temperature, values with different superscripts differ ($P<0.05$), indicating a treatment effect.

X,Y,Z: within a treatment, values with different superscripts differ ($P<0.05$), indicating a temperature effect.

Figure 4A:
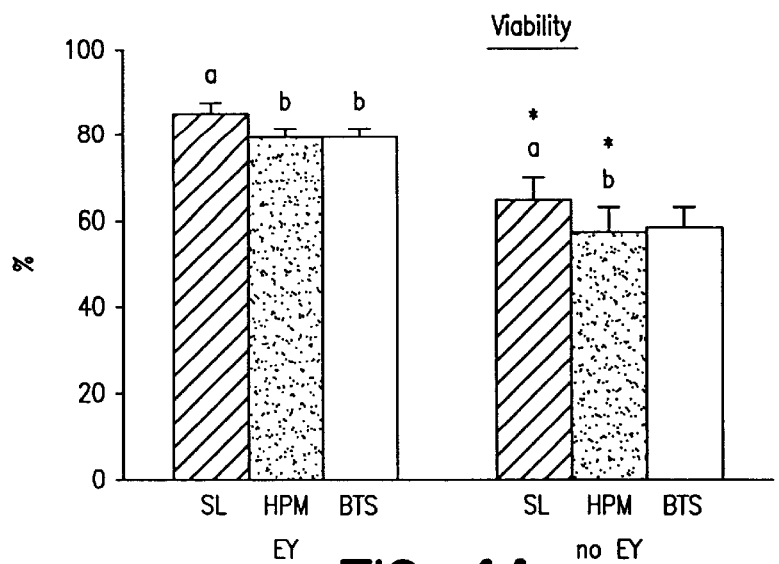
Figure 4B:
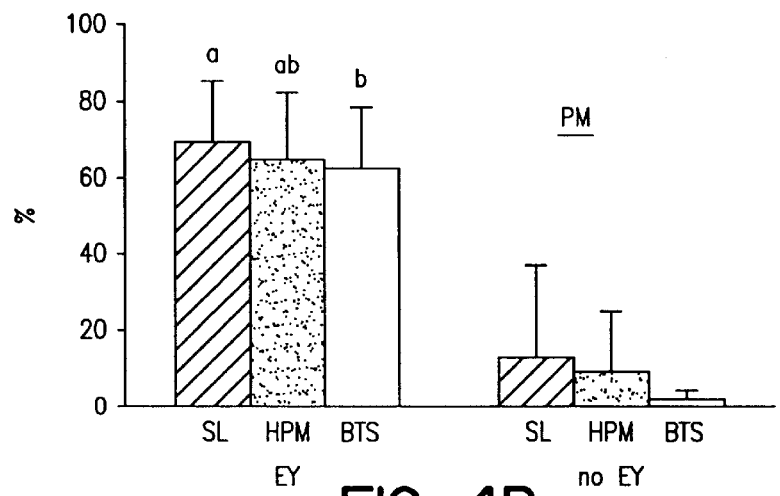
Figure 4C:
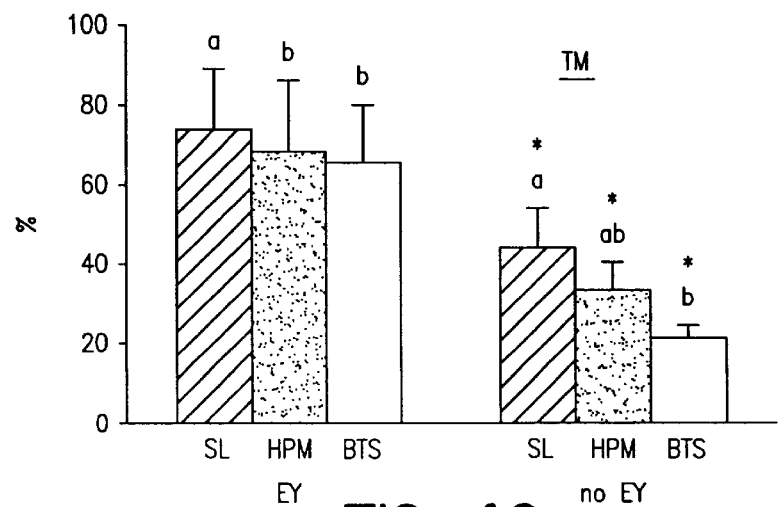

FIG. 4. Impact of lipids on sperm function (mean±SE, n=4) immediately after addition of extender±20% egg yolk and surfactant (EY) at 24 C. SL, Select lipids; HPM, head plasma membrane lipids; BTS, extender control.

a,b,c: within EY or no EY, values with no superscripts in common differ ($P<0.05$).

*:differs from corresponding treatment with EY. Statistical analysis performed on transformed data (see Materials and Methods).

Figure 5A:
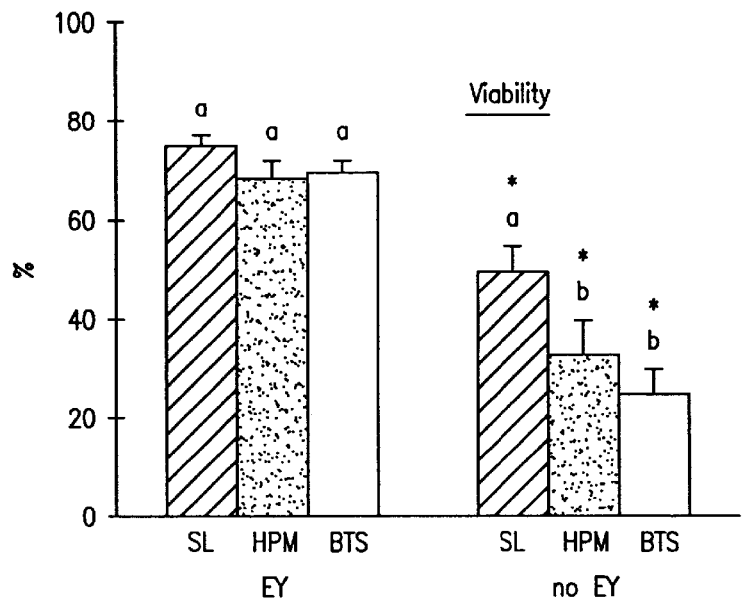
Figure 6A:
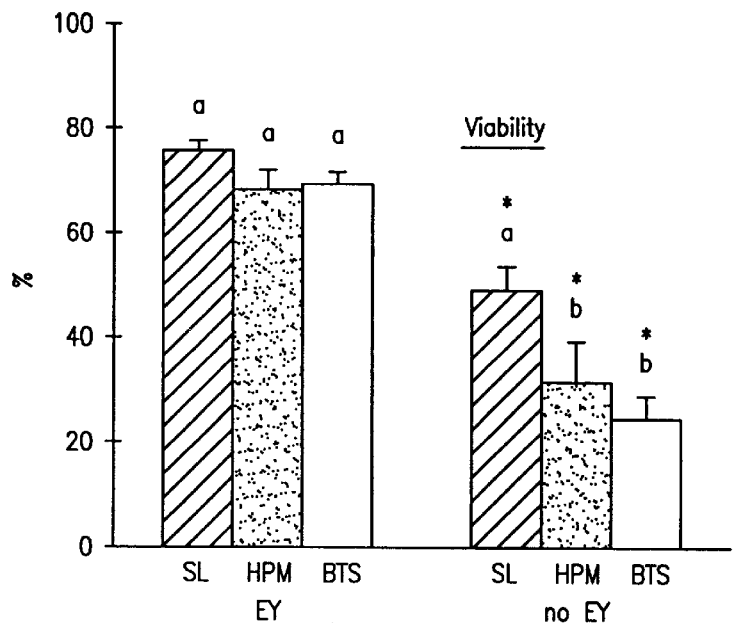
Figure 6B:
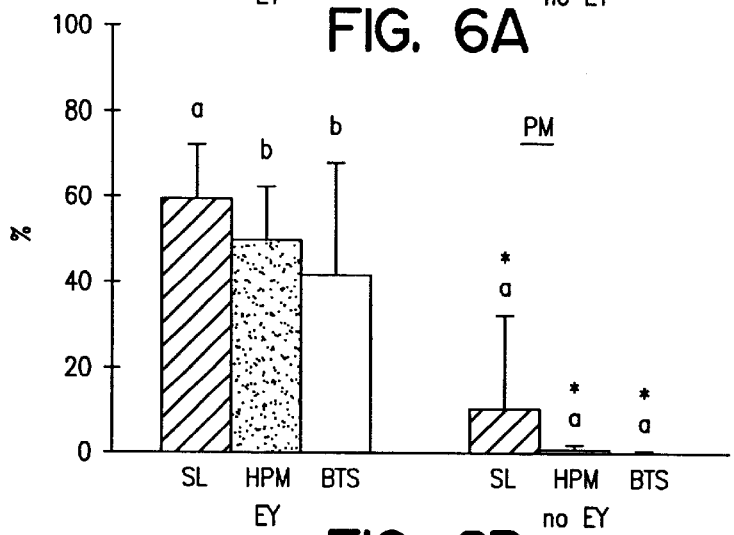
Figure 6C:
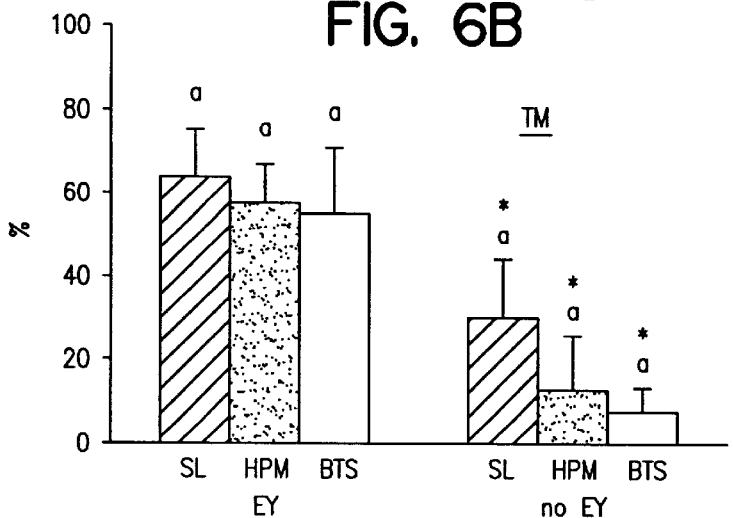

FIG. 5. Impact of lipids on sperm function (mean±SE, n=4) after cooling to 5 C. SL, Select lipids; HPM, head plasma membrane lipids; BTS, extender control.

a,b,c: Within EY or no EY, values with no superscripts in common differ (P<0.05).
*differs from corresponding treatment with EY. Statistical analysis performed on transformed data (see chapter II Materials FIG. 6. Impact of lipids on sperm function (mean±SE, n=4) immediately after addition of extender B (final concentration, 3% glycerol) at 5 C. SL, Select lipids; HPM, head plasma membrane lipids; BTS, extender control.
a,b,c: within EY or no EY, values with no superscripts in common differ (P<0.05).
* differ from corresponding treatment with EY. Statistical analysis performed on transformed data (see Materials and Methods).

Figure 7A:
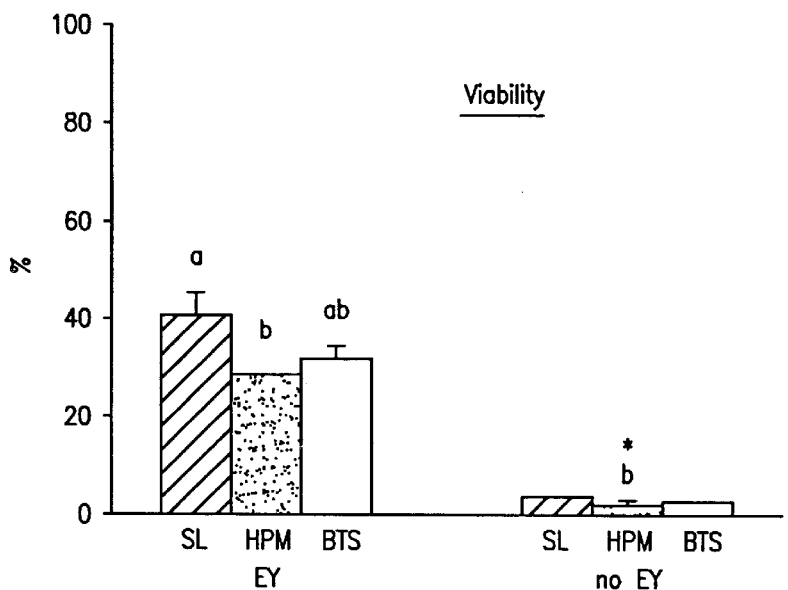
Figure 7B:
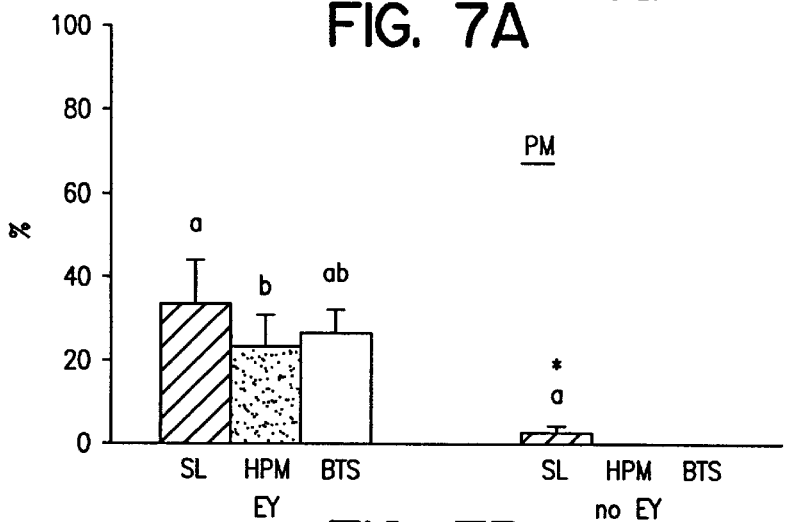
Figure 7C:
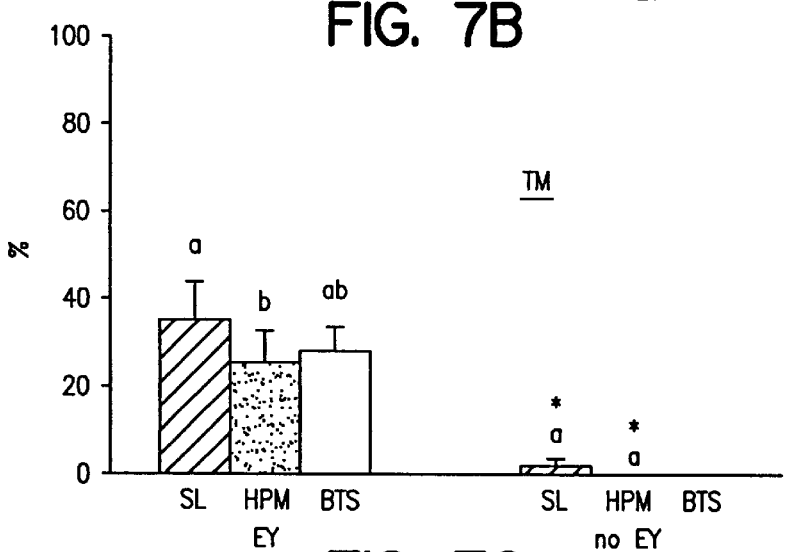

FIG. 7. Impact of lipids on sperm function (mean±SE, n=4) after thawing in 0.02M Caffeine in BTS. SL, Select lipids; HPM, head plasma membrane lipids; BTS, extender control.
a,b,c within EY or no EY, values with no superscripts in common differ (P<0.05).
*:differ from corresponding treatment with EY. Statistical analysis performed on transformed data (see Materials and Methods).

DETAILED DESCRIPTION OF THE INVENTION INCLUDING BEST MODES

We identified and characterised the incorporation of exogenous lipids into sperm, and determined the effect that the lipids had on sperm function during cryopreservation. The experiments below show that
1. Exogenous lipid SUVs fuse to sperm at 35° C., at a neutral pH and without any fusogenic factors.
2. Fusion efficiency is affected by sperm concentration, lipid type, and incubation time.
3. The select lipids (SL) used in the invention have beneficial effects on boar and bovine sperm viability during cooling.
4. SL lipids in the presence and absence of egg yolk improve post-thaw sperm function.

We are testing modifications to the original SL recipe (modifications being tested include, but are not limited to, altered ratio of particular phospholipid head groups, altered ratio of fatty acids within one or more phospholipids, addition of other chemical types of lipids such as glycerolipids and sterols) in boar semen. For all modifications, we first quantitate fusion rates and then cryopreserve semen from at least 4 males and test viability and motility in multiple replicates of control and lipid-treated sperm before, during, and after the cooling and freezing process. These modifications will improve the preservative effect of the lipids. We are testing the impact of these lipids on the in vitro fertilising ability of the sperm. They will not deleteriously affect the performance of sperm in this important commercial reproductive technology.

EXAMPLE 1
Boar Sperm Preservation

We adjusted the SL concentration to obtain a maximal post thaw result. We examined the SL effect on acrosome membrane integrity and fertilizing ability, besides the sperm viability and motility. We adjusted the composition of SL with consideration of including cholesterol and lipoprotein in liposome.

To investigate the ability of treated boar sperm to fertilize we have or plan to observe:
1) The ability of sperm to capacitate and acrosome react based on the CTC stain.
2) The ability of sperm to fertilize in vitro
3) The ability of sperm to fertilize in vivo In all three experiments, we utilised untreated sperm, sperm treated with HPM lipids, and sperm treated with SL lipids (as detailed above).

To alter SL composition, we sequentially altered the relative amounts of the various lipids in the SL liposomes and evaluate sperm viability during cooling and cryopreservation:
1) Altered the relative proportions of the phospholipids in SL, while maintaining the fatty acid compositions as stated in the thesis.
2) Added cholesterol at three levels to the SL, while leaving the phospholipids in the same relative proportions as described. We are investigating the inclusion of cholesterol (alone or attached to a protein) on SL function.
3) Will alter the fatty acid content of the phospholipids in SL, first by increasing the relative proportion of unsaturated fatty acids in all phospholipids.

We will investigate the properties of egg yolk and its interaction with sperm membranes±SL. We will determine the degree of incorporation of egg yolk into boar sperm using R18 measured in a flow cytometer. Egg yolk is included at the same concentration as the SL and HPM lipids were in experiment I and then when mixed with varying proportions of the SL SUVs, and we determine incorporation in the presence and absence of 0 and 1 mM $Ca^{2+}$ and with $10^7$ and $10^8$ sperm/ml.

Fifteen kinds of phosphatidyl and sphingomyelin lipids with specific fatty acid chains were tested. One skilled in the art could vary the types of phosphatidyl and sphingomyelin lipids and specific fatty acid chains without departing from the scope of the invention. The compositions below and the types of phosphatidyl and sphingomyelin lipids with specific fatty acid chains in these compositions illustrate the best mode of making and using the invention.

|  | Purity | Supplier |
| --- | --- | --- |
| PC: | | |
| L-a-phosphatidylcholine, Dipalmitoyl (16:0) | 99% | Sigma |
| L-a-phosphatidylcholine, Disteroyl (18:0) | 99% | Sigma |
| L-a-phosphatidylcholine, Dioleoyl (18:1) | 99% | Sigma |
| L-a-phosphatidylcholine, Dilinoleoy (18:2) | 99% | Sigma |
| L-a-phosphatidylcholine, Diarachidonoyl (20:4) | >99% | Avanti |
| L-a-phosphatidylcholine, Diheptadecanoyl (22:6) | >98% | Matreya |
| PE: | | |
| L-a-phosphatidylethanolamine, Dipalmitoyl (16:0) | 99% | Sigma |
| L-a-phosphatidylethanolamine, Disteroyl (18:0) | 99% | Sigma |
| SPH: | | |
| Natural sphingomyelin (egg) (77.7% 16:0) | >99% | Avanti |
| N-stearoyl-a-sphingomyelin (18:0) | 99% | Sigma |
| PS: | | |
| Dl-a-phosphatidyl-1-serine, Dipalmitoyl (16:0) | 99% | Sigma |
| Dl-a-phosphatidyl-1-serine, Distearoyl (18:0) | >99% | Avanti |
| Dl-a-phosphatidyl-1-serine, Dilinoleoyl (18:2) | >99% | Avanti |
| PI: | | |
| Natural PI (plant) (36% 16:0) | 98% | Matreya |
| L-a-PI (liver) (41.33% 18:0, 10.71% 18:1) | >99% | Avanti |

One aliquot of dry HPM lipids (about 20 mg) was dissolved in chloroform-methanol CM to the concentration of 20 ug/ul. To prepare one batch of 16 ml SUVs with 0.6930 umole lipids/ml (Mol. Wt: 617), 42.76 ul of HPM lipid solution was pipetted into each of eight screweapped tubes (1.5×15 cm). 0.02829 umole of R18 (final concentration=2 mole % of lipids) was added into each tube. Samples were dried under $N_2$ for 10 minutes and in the vacuum dessicator for 30 minutes, then rehydrated with 60° C. Beltsville Thawing Solution (BTS, pH 7.3) buffer and vortexed (3×20") to dissolve the lipid films that were on the wall of the test tubes. The tubes were filled with $N_2$ and capped tightly with a layer of parafilm, then sonicated at room temperature for 30 minutes. Finally, samples were frozen and stored under $N_2$ in −70° C. for no more than one week. Before use, each aliquot was thawed at 25° C., its pH adjusted to 7.3 and resonicated for 30 minutes. The final lipid concentration was 0.3465 umole/ml.

SUVs were prepared using proportions of phospholipids based on differences in membrane lipids caused by cryopreservation (Buhr et at., 1994). These proportions were:
PC:PE:SPH:PS:PI=21.05:26.32:42.11:5.26:5.26. These proportions can be varied by one skilled in the art without departing from the scope of the invention.
a. Proportion (mol %) of PC with specific fatty acid chains were: C16: 0=7.37%, C18: 0=3.16%, C18: 1=5.26%, C18: 2=3.79%, C20: 4=0.84%, C22: 6=0.63%
b. Proportion (mol %) of PE with specific fatty acid chains were: C16: 0=5.26%, C18: 0=21.06%
c. Proportion (mol %) of SPH with specific fatty acid chains were: C16: 0=15.97%, C18: 0=25.27% C22: 6=5.34%
d. Proportion (mol %) of PS with specific fatty acid chains were: C16: 0=0.53%, C18: 0=4.21%, C18:2=0.53%
e. Proportion (mol %) of PI with specific fatty acid chains were: C16: 0=0.62%, C18: 0=6.22% C18: 1=0.20%, C18:2=0.62%

These proportions can be varied by one skilled in the art without departing from the scope of the invention. The preparation and the concentrations of select lipids (SL) and R18 were the same as those for HPM lipid SUVs.

Two $Ca^{++}$ concentrations (0 and 1 mM $CaCl_2$ in $H_2O$), two sperm concentrations ($10^7$ and $10^8$ sperm/ml in final reaction mixture) and two kinds of lipid SUVs (HPM and SL, 0.3119 umole/ml in final reaction mixture) were used to determine the effects of these factors on fusion efficiency.

Fusion efficiency was tested by altering sperm concentration and calcium or each lipid type, as shown in Table 1. Tubes were incubated at 34 C. The final concentrations of sperm were $1\times10^7$ and $1\times10^8$ sperm/ml; the concentrations of $Ca^{++}$ were 1 mM and 0 mM, and the lipid concentration was 0.3119 umole/ml; final volume was 1000 ul.

TABLE 1

Experimental arrangement for flow cytometric assessment of fusion efficiency of liposomes (SUV) with porcine spermatozoa. Liposomes were made with either HPM or select lipids (final concentration: 0.3119 umol/ml). R18 was included at 2 mol %. For each type of SUV, n = 3.

| Cuvette | 1 | 2 | 3 | 4 |
|---|---|---|---|---|
| SUV/R18 | + | + | + | + |
| $Ca^{++*}$ | 1 | 1 | 0 | 0 |
| Sperm (×$10^8$) | 1 | 0.1 | 1 | 0.1 |

*: $Ca^{++}$(1 mM) or $H_2O$ (0) was added at 0.1 minute.

In preliminary trials, boar sperm and SUVs/R18 were read individually in the flow cytometer (Coulter Epics Elite ESP, MI. USA) to establish the proper cytometer settings. With the excitation and emission wavelengths set at 488 and 570–580, the voltage of forward scale was adjusted to 550 volts to have the sperm population completely on the scale, and the voltage of fluorescent intensity was adjusted to 600 volts to obtain the maximum separation of sperm and SUV/R18 populations in the histogram.

For each replicate, before incubation began, sperm and SUV/R18 were run through the flow cytometer to check the distribution of these populations using the program outlined above. Then $Ca^{++}$ (0 or 1 mM) was added and the reaction started with the addition of sperm or BTS (time=0). Samples were maintained at 34° C. in a water bath. At 1, 10, 30, and 60 minutes, 100 ul was taken from each treatment tube, diluted to $1\times10^6$ with BTS buffer and injected into the flow cytometer.

To determine the effect of lipid on sperm viability during cooling, 2 ml of the frozen SUVs of HPM lipids or SL were thawed at 25° C. and the pH adjusted to 7.3. The concentration of total lipids in this solution was 0.3465 umole/ml. These SUV solutions were then resonicated for 30 minutes at room temperature, filled with $N_2$ and stored in the dark at room temperature for a maximum of 60 min before addition to sperm.

All steps were conducted at 35–36° C. Semen samples were collected from two boars for each replicate (n=3) and identical numbers of sperm were combined after the concentration reading. The pooled sperm were filtered through a double layer of Miracloth. After filtration semen was diluted with BTS solution to $1\times10^8$ sperm/ml.

A programmable bath (Biocool II. FTS System Inc.) was employed to achieve the desired cooling rate of 0.1 C./min and each temperature holding point as described in the cooling procedure (FIG. 1). Cooling rate was established in the semen sample tube in a preliminary experiment.

Before the start of cooling, 1800 ul of HPM, SL or BTS buffer were pipetted into three cork plugged test tubes (12×75 mm) and placed in the cooler at 34° C. for 20 minutes to warm the solution. BTS diluted semen (200 ul, $1\times10^8$ sperm/ml) was added to each of these three tubes after 20 min (t=0) and cooling was started. The final concentrations of lipids and sperm were 0.3119 umole/ml and $1\times10^7$ sperm/ml. During slow cooling, 500 ul of this reaction mixture was taken from each reaction tube at 34° C. (t=0), 24° C. (t=100), and 5° C. (t=300) for viability testing.

To determine the effects of cold shock, 500 ul of reaction mixture from each of these three tubes at 28° C. (t=60 minutes) was pipetted into 1500 ul microcentrifuge tubes, which were plunged into ice water. Once the samples had reached 0–5° C. (4–5 minutes), they were held at that temperature for 5 minutes, and then tested for viability. To determine the effect of lipid on viability and motility of sperm during freezing-thawing SUVs (HPM and SL) were prepared as described above.

Two kinds of freezing extender were prepared. One was the original Beltsville F5 extender (Appendix 1, Table 1) which includes egg yolk and Orvus ES paste (Extender 1), and the other was Beltsville F5 extender without egg yolk and Orvus ES paste (Extender 2).

Semen was cooled and frozen. For each replicate, 3.6 ml of SUV solution was put into tubes one and two (SL) and tubes three and four (HPM), while tubes five and six received BTS as a control. All tubes were incubated at 34° C. for 20 mins. Each tube then received 400 ul of pre-diluted sperm ($1\times10^8$ sperm/ml); the final concentrations of lipids and sperm were 0.3119 umole/ml and $1\times10^7$ sperm/ml. These mixtures were cooled to 24° C. at 0.1 C./min in the Biocooler and then centrifuged (800×g, 10 min, 24° C.). Sperm pellets were resuspended with Fraction A of the extenders to the volume before centrifuging. Tubes 1, 3 and 5 received Fraction A of Extender 1, while tubes 2, 4, 6 received Fraction A of Extender 2. These suspensions were cooled to 5° C. (0.1 C./min). The Fraction B of the extenders (5° C.; 1:1 vol:vol) were then added into the corresponding tubes and mixed with transfer pipette.

All equipment and materials which included sealing machine, labelled straws, straw holders, tubes for filling semen and forceps were pre-cooled in a 5° C. room for 2 hours before use. After Fraction B of extender was added, semen samples were loaded into 0.5 cc straws (Ca# AA 101 IMV International Corp., Minneapolis, Minn. USA) and sealed with stainless steel sealing balls. An adjustable perforated steel shelf (29 cm in diameter) was set up 21.5 cm above the surface of liquid nitrogen. The straws were put on the shelf, the nitrogen container covered with a styrofoam cover, and the straws were frozen for 3 min exactly. This process included cooling from 5° C. to −2° C., a pause at −2° C. for 30 seconds (super cool), and from −2° C. to −70° C. with a cooling rate of 30° C./min, as determined by placing a thermocouple into a filled straw (Pettitt, 1996). Straws were then immediately plunged into liquid nitrogen. The straws from all samples were transferred into a liquid nitrogen storage tank and held for at least three days before quality tests.

Straws were thawed by gently agitating the intact straws in 60° C. water bath for 5 seconds. Both ends of each straw were cut and semen was incubated in pre-warmed 37° C. BTS/Caffeine (Caffeine 0.02 M) for ten minutes.

Samples (500 ul for viability test, 50 ul for motility test) were taken from each treatment at: 34° C. within one min after addition of SUVs; 24° C. before centrifugation; 24° C. after addition of Fraction A; 5° C. before addition of Fraction; 5° C. after addition of Fraction B; and after thawing. The post-thaw semen samples were incubated with BTS(Caffeine solution during viability staining and motility counting.

Cell populations (sperm, SUV) in the sample were scattered according to cell size (Forward Scale) and fluorescent intensity of cell surface. Solutions of either diluted sperm suspension or SUVs/R18 were run through the flow cytometer and provided the basic scatter plot of particle in the sperm population and SUV/R18 population.

[AS1]From data quantified as number of sperm with incorporated lipids, sperm with no incorporated lipids and free SUVs, fusion efficiency was calculated as: % of sperm with incorporated.

Fusion Efficiency

Figure 2:
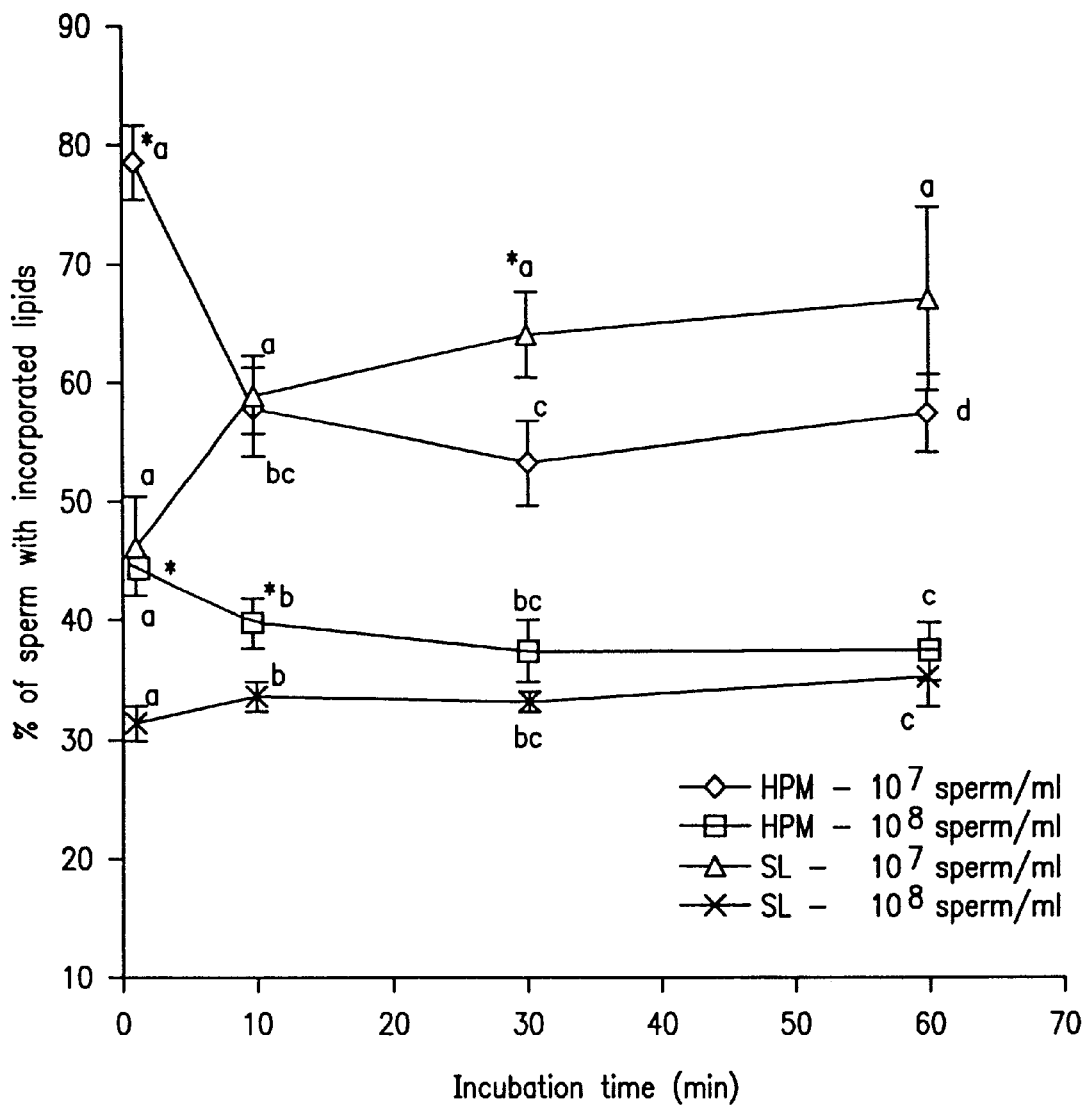
FIG. 2. Percentage of sperm with incorporated lipids over time (mean±SE) as measured by flow cytometry. Boar sperm (pooled data, n=3) at $10^7$ or $10^8$ sperm/ml were incubated at 35 C. with R18-labelled liposomes (SUV) made with HPM or SL and fusion measured by flow cytometry. The % sperm with incorporated lipids was higher for $10^7$ than $10^8$ sperm/ml ($P<0.05$) at all times.

Fusion efficiency did not differ between 0 and 1 mM $Ca^{++}$ for either lipid or sperm concentration at any time ($P>0.05$; Appendix 2, Table 1). Therefore values for 0 and 1 mM $Ca^{++}$ were pooled for determination of the effect of lipids, concentration and time. HPM lipids fused to sperm faster than SL at both sperm concentrations (FIG. 2).

The percentage of sperm with fused HPM lipids did not increased after 1 minute. With $10^7$ sperm/ml, the percentage declined after 1 minute ($P=0.0014$), and then maintained this lower level for at least 60 minutes. With $10^7$ sperm/ml, percentage of sperm with incorporated SL was lowest at t=0 minute. This value increased by t=10 ($P<0.05$), and remained constant to the end of incubation (analysis was conducted on the pooled 0 and 1 mM $Ca^+$ data, FIG. 2). For both lipids, more sperm in the $10^7$ concentration had lipids fused ($P<0.05$). By 60 minutes, both HPM and SL had fused to the same percentage of sperm at each sperm concentration.

Boar Sperm Viability

Boar sperm viability changed during the cooling process. Lipid treatments significantly affected the pattern of change (FIG. 3, Table 2). At 34° C., viabilities in the SL treatments were lower than those in control (BTS) and HPM groups ($P<0.05$). Viability of SL-treated sperm did not change ($P=0.4297$) after cooling to 24° C. (Table 2), while the viability of both HPM- and BTS-treated sperm declined ($P<0.005$). Cooling to 5° C. reduced viability in all treatments, but SL-treated sperm suffered the least loss (FIG. 3) and absolute viabilities ranked SL≡HPM>BTS (FIG. 3; $P<0.05$). The total loss in viability from 34 to 5° C. in SL-treated sperm was much less than for HPM-treated sperm, which was in turn significantly less than that undergone by the BTS control (Table 2).

Cold-shock Test

For the cold-shock test, sperm viability was dramatically decreased in both treatments (SL: 2.8±1.2%, HPM: 3.7±1.3%) and control (4.7±1.8%) and no significant differences were found between SL and HPM ($P=0.3700$), SL and BTS ($P=0.0953$) and HPM and BTS (0.3086).

TABLE 2

Percentage change in viability during cooling (n = 3).
Viability (% live sperm) was determined at 34° C., 24° C. and 5° C. with fluorescent microscopy on sperm stained with SYRR-14 and Propidium Iodide. The % change of viability between temperatures was defined as the proportional difference in viability (V) between the lower and higher temperature ($V_{low}$-$V_{high}$/$V_{high}$X 100%). Statistical analysis was conducted on arsine transformed data. Values in each column (mean ± SE) with no superscript in common differ (P < 0.05).

| Treatment | 34° C.–24° C. | 24° C.–5° C. | 34° C.–5° C. |
|---|---|---|---|
| SL | 2.0 ± 5.1$^a$ | −10.0 ± 3.9$^a$ | −8.0 ± 3.8$^a$ |
| HPM | −12.5 ± 3.5$^b$ | −5.6 ± 1.5$^a$ | −18.0 ± 4.6$^b$ |
| BTS | −19.2 ± 4.8$^b$ | −17.4 ± 5.0$^b$ | −36.6 ± 1.5$^c$ |

As the result of full model test, the overall effects of lipid, egg yolk and temperature on viability, progressive motility and total motility were highly significant ($P<0.01$). There was no interaction between lipid and egg yolk ($P>0.05$).

At 34° C., after sperm had incubated with their treatments for 1 min, viability was significantly lower in SL than in HPM or BTS (Table 3., $P<0.05$). Progressive motility (PM) was higher in SL than in either HPM or BTS ($P<0.05$), but total motilities (TM) were not different among treatments.

TABLE 3

Impact of lipid on the viability, progressive motility (PM), and total motility (TM) of boar sperm at 34C (mean ± SE, n = 4). Boar sperm ($10^7$ sperm/ml) was incubated with liposomes made with SL or HPM lipids (0.3119 umole/ml) or BTS at 34C. Immediately, 500 ul and 50 ul for each of these mixtures were taken for viability (SYBR-14 and Propidium Iodide) and motility evaluation. Data from duplicate tubes in each treatment were pooled. Statistical analysis was conducted on transformed data (see Materials and Methods). Within a trait, treatments with no superscripts in common differ (P < 0.05).

| Treatment | Viability | PM | TM |
|---|---|---|---|
| SL | 82.5 ± 0.7$^a$ | 15.6 ± 4.3$^a$ | 77.9 ± 1.3$^a$ |
| HPM | 83.8 ± 0.8$^b$ | 7.6 ± 4.8$^b$ | 71.0 ± 4.7$^a$ |
| BTS | 85.4 ± 0.8$^b$ | 10.1 ± 5.3$^b$ | 73.6 ± 4.7$^a$ |

At 24° C., before extender A was added, treatments influenced the % of viable sperm (Table 4; SL>RPM>BTS, $P<0.05$), PM (SL>HPM=BTS) and TM (SL>HPM>BTS, $P<0.05$).

TABLE 4

Impact of lipid on the viability, progressive motility (PM), and total motility (TM) of boar sperm at 24C (mean ± SE, n = 4). Boar sperm ($10^7$sperm/ml) were incubated with liposomes of SL or HPM lipids (0.3119 umole/ml) or BTS at 34C. Samples were cooled to 24C at 0.1C per minute, when 500 ul and 50 ul for each sample was taken for viability (SYBR-14 and Propidium Iodide) and motility evaluation, respectively. At this stage, data from each trait were pooled from duplicate tubes in each lipid treatment, which were designed to receive the two extenders in following step. Statistical analysis was conducted on transformed data (see Materials and Methods).. Within a measure, treatments with no superscripts in common differ (P < 0.05).

| Treatment | Viability | PM | TM |
|---|---|---|---|
| SL  | 79.0 ± 1.0[a] | 11.8 ± 4.3[a] | 74.1 ± 1.0[a] |
| HPM | 74.6 ± 1.3[b] | 5.4 ± 3.4[b]  | 68.2 ± 2.6[b] |
| BTS | 61.3 ± 2.1[c] | 5.9 ± 2.8[b]  | 59.7 ± 2.9[c] |

Immediately after adding extender A at 24° C., the overall effect of egg yolk was highly significant (model test, P=0.0001), and viability, PM and TM in the presence of EY was significantly (P<0.05) higher regardless of treatment (FIG. 4). To determine the effect of each lipid more clearly, data were divided into EY and no-EY groups.

In the presence of egg yolk, viability (FIG. 4A) was significantly (P<0.05) higher with SL than either HPM or BTS; progressive motility for SE (FIG. 4B) exceeded BE (P<0.05), while HE was intermediate. Total motility was similar between SL and HPM but higher than BTS. In the absence of egg yolk, SL resulted in higher viability and motility than either HPM or BTS (P<0.05). Progressive motility was similar among treatments.

At 24° C., sperm functions changed within each lipid treatment after addition of extender A. In comparison to values at 24° C. immediately before addition of the extender. viability increased in SL (P=0.0263) and in BTS (0.0001) with the addition of EY but decreased in SL and HPM with no EY (P<0.05). In the presence of EY, progressive motility greatly increased in all treatments (P=0.0001), although total motility was not changed in any of these treatments. However in the absence of the EY, total motility dropped dramatically in these treatments (SL, BTS: P=0.0001, HPM P=0.002).

After cooling to 5° C., the overall effect of egg yolk was significant (model test, P=0.0001), and viability, PM and TM in treatments with EY was significantly (P<0.05) higher than any comparable treatment without EY (FIG. 5). To determine the effect of each lipid more clearly, data were divided into EY and no EY groups.

Figure 5B:
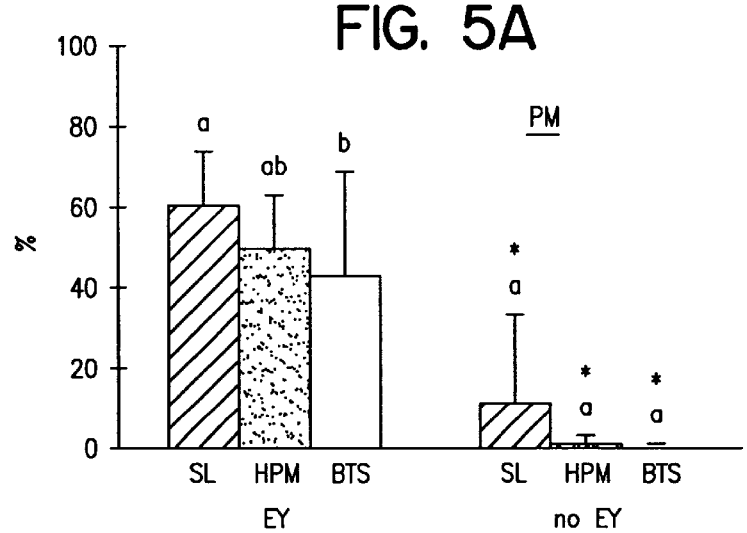
Figure 5C:
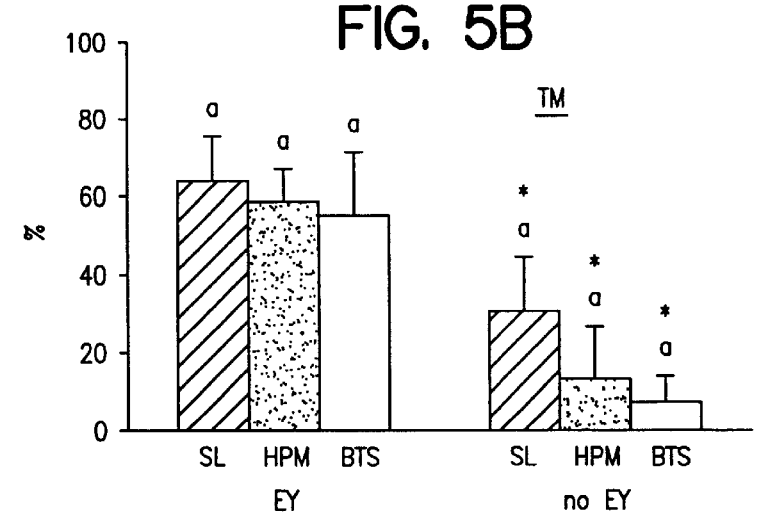

In the presence of egg yolk, PM was higher (P<0.05) for SL than BTS, while HPM was intermediate (FIG. 5B). TM in SL was similar to HPM but higher than BTS (P<0.05) (FIG. 5C). Viability was similar among three treatments. In the absence of egg yolk, viability and motility were higher (P<0.05) in SL Immediately after adding extender B at 5° C., the overall effect of egg yolk remained highly significant (model test P=0.0001), and treatment with EY was significantly higher than any comparable treatment without EY (P<0.05, FIG. 7). To determine the effect of each lipid more clearly, treatments were divided into EY and no EY groups.

As with values before the addition of extender B, in the EY group the PM in SL-treated sperm was better than BTS, and in the no EY group, viability and TM of SL-treated sperm were higher than the other treatments. Values for all other traits were similar (FIG. 7). Traits did not change immediately after addition of extender B, except for a decrease in the viability of the BTS no EY treatment (P=0.0193).

Again, egg yolk effect was significant (model test, p<0.0001), and viability, PM and TM higher (P<0.05) with EY than without (FIG. 7). For sperm cryopreserved in the presence of egg yolk, viability, PM and TM were significantly higher (P<0.05) in SL than HPM, with values for the BTS industry-standard being intermediate (FIG. 7. A.B.C). In the absence of egg yolk. SL significantly (P<0.05) improved viability, progressive and total motility.

When post-thaw data were compared to values obtained at 5° C. after addition of extender B, viability, PM and TM had decreased in all treatments which included EY (P=0.0003). In the no EY group, viability and TM was decreased in SL-treated sperm (P=0.0001 and 0.0302, respectively), while only viability was decreased in HPM (P=0.0256). All other values in the HPM and BTS treatments in the absence of EY had been essentially zero at 5° C., and so could not decrease further.

EXAMPLE 2

Preservation of Bull Sperm

Lipid/CM solutions were mixed in the exact proportions described previously for boar sperm; dried under $N_2$ and then in a vacuum dessicator for 30 min and then rehydrated with 60 C. CSN/tris buffer (pH 7.3) and vortexed (3×20") to dissolve the lipid films which were on the wall of the container (1.5×15 cm screw-capped tubes). The lipid concentration in the buffer was 0.693 μmol/ml.

In a preliminary trial with semen from 4 bulls, semen was prepared, cooled and frozen. A second trial used three bulls, (familiarly named Dynasty, Gypco and Warrior) and semen was treated and frozen at the commercial bull AI company, Gencor. The sperm concentrations for the second trial were $2.162 \times 10^9$, $1.862 \times 10^9$ and $1.736 \times 10^9$ sperm/ml respectively. For both the preliminary and second trial, semen was kept at 35° C. The concentrations were adjusted to $2 \times 10^9$ sperm/ml by centrifugation (500×g, 10 min, 35° C.) or dilution (35° C. CSN/tris buffer).

At 35° C., for each bull three 15 ml centrifuge tubes were prewarmed for 10 min. Two tubes contained 1800 μl of lipid solution (SL) and the third tube contained 1800 μl CSN/tris buffer with no lipids, as a lipid blank; this blank is the same as the normal industry method of preparing semen. Semen prepared above (200 μl, $2 \times 10^9$ sperm/ml) was added into each of these three tubes for each bull, giving two SL plus the blank. These samples were transferred to a 32° C. water-bath and incubated for 20 min. CSN/tris buffer containing egg yolk (2 ml) were added to one SL (SL+EY) tube and the blank (CON). The second SL tube received 2 ml CSN/tris minus egg yolk (SL−EY). All samples were cooled to 5° C. over 120 min. In the preliminary trial, semen was sampled repeatedly during the cooling process.

At 5° C, semen samples were filled in 0.25 ml transparent straws, sealed and frozen with programmable machine. The freezing rates were 4° C./min (5° C. to −12° C.), −10 C./min (−12° C. to −40° C.) and −40° C./min (−40 to −140° C.). After the straws were cooled to −140° C., they were plunged into liquid $N_2$ (−196). Straws were stored at least three days before quality examination.

Straws were thawed by plunging the intact straws into a 37° C. water bath for 60 seconds. Both ends of each straw were then cut; semen was incubated and diluted to 0.5 to $1 \times 10^7$ sperm/ml in pre-warmed 37° C. CSN-tris buffer.

For checking the sperm motilities, subjective microscopy (400×) counting and computer assisted sperm analysis (CASA) techniques were used.

TABLE 5

Experiment I using Bull sperm

| Bull | Initial | 35 C V SL[A] + EY[B] | 35C V CON[C] | 35C V SL − EY | 5C V SL + EY | 5C V CON | 5C V SL − EY | Post Thaw V SL + EY | Post Thaw V CON | Post Thaw V SL − EY | Post Thaw M (P/T) SL + EY | Post Thaw M (P/T) CON | Post Thaw M (P/T) SL − EY |
|---|---|---|---|---|---|---|---|---|---|---|---|---|---|
| Sandstone | 78.7 | 74.5 | 79.2 | 77.2 | 66.5 | 51.8 | 60.3 | | | | | | |
| Dinasty | 73.1 | 70.6 | 74.3 | 77.0 | 75.3 | 61.4 | 49.1 | 26.5 | 15.9 | 10.2 | | | |
| Leo | 85.1 | 78.6 | 78.3 | 82.1 | 84.2 | 78.1 | 73.5 | 17.0 | 14.1 | 2.8 | 20 | 20 | 4 |
| Dinasty | 87.1 | 79.7 | 68.2 | 77.2 | 76.5 | 77.3 | 66.9 | 35.3 | 33.8 | 12.7 | 23.8 | 26.8 | 8 |
| mean | 81 | 75.9 | 75 | 78.4 | 75.6 | 67.2 | 62.5 | 26.3 | 21.3 | 8.6 | 22 | 23 | 6 |

V = Viability, M = Motility
A; SL, sperm lipids
B; EY, egg yolk
C; control

TABLE 6

Microscope motility counting of bull sperm

| Bull | SL + EY | CON | SL − EY |
|---|---|---|---|
| a. progressive motility (%), mean ± SE of 4 straws/trt for each bull | | | |
| Gypco | 51.2 ± 2.1 | 38.4 ± 2.4 | 6.3 ± 1.3 |
| Warrior | 55.6 ± 2.2 | 43.8 ± 3.8 | 8.1 ± 0.7 |
| Dynasty | 48.7 ± 5.3 | 50.0 ± 4.4 | 14.3 ± 2.2 |
| Mean | 51.5 ± 2.1[a] | 44.1 ± 2.4[b] | 9.6 ± 1.3[c] |
| b. total motility (%) mean ± SE for 4 straws/trt for each bull | | | |
| Gypco | 54.5 ± 2.8 | 42.2 ± 2.7 | 9.9 ± 1.2 |
| Warrior | 58.7 ± 1.9 | 47.4 ± 4.0 | 12.4 ± 1.4 |
| Dynasty | 52.3 ± 5.0 | 53.9 ± 4.0 | 19.3 ± 2.5 |
| Mean | 55.1 ± 2.0[a] | 47.8 ± 2.4[b] | 13.9 ± 1.5[c] |

[a,b,c]values differ, P < 0.01

TABLE 7

CASA total motility (%) Mean ± SE of 2 straws/trt

| Bull | SL + EY | CON | SL − EY |
|---|---|---|---|
| Gypco | 41.6 ± 4.2 | 43.7 ± 0.2 | 9.0 ± 0.2 |
| Warrior | 46.6 ± 4.2 | 25.2 ± 0.9 | 7.8 ± 3.9 |
| Dynasty | 41.0 ± 2.7 | 33.0 ± 1.1 | 16.7 ± 4.9 |
| Mean | 43.1 ± 2.1 | 34.0 ± 3.4[b] | 11.2 ± 2.4[c] |

[a,b,c]values differ, P < 0.05

TABLE 8

Viability (%) Mean ± SE of 4 straws/trt

| Bull | SL + EY | CON | CSN − EY |
|---|---|---|---|
| Gypco | 39.7 ± 4.2 | 31.5 ± 4.9 | 13.6 ± 4.0 |
| Warrior | 49.1 ± 6.4 | 38.1 ± 5.6 | 16.1 ± 4.1 |
| Dynasty | 40.2 ± 6.4 | 41.6 ± 5.3 | 22.0 ± 2.7 |
| Mean | 43.0 ± 3.3[a] | 37.0 ± 3.0[b] | 17.2 ± 2.2[c] |

[a,b,c]:Values differ, P < 0.05

These experiments show that bull sperm take up the SL avidly and, depending on the bull, either improve or do not harm the viability and motility of cryopreserved sperm. In Table 5, the mean post-thaw viability was 26% as compared to 21%, which amounts to a (5/21×100%) 20% increase in survival rate. The more complete trial with three bulls (Tables 6,7 and 8) all clearly demonstrate an improvement for two of the three bulls of the same magnitude, while the third bull showed no change.

The present invention showed that incorporation of selected lipids improves the survival of boar and bull spermatozoa following cryopreservation. Liposomes were made from lipids extracted from head plasma membrane (HPM) of boar spermatozoa or from selected lipids (SL) which contained specific phospholipids. At a fixed lipid concentration, fusion efficiency with spermatozoa as measured by flow cytometry and R18 dequenching was affected by lipid type, sperm concentration and incubation time.

SL and HPM improved sperm viability (SYBR-14 and propidium iodide) and motility during cooling to SC, with SL±egg yolk better than or equal to HPM (P<0.05). Post-thaw, egg yolk showed a strong cryoprotective effect. Compared to HPM, SL-treated sperm had higher post-thaw viability, progressive motility and total motility in the extender including egg yolk and higher viability in the extender excluding egg yolk (P<0.05).

The invention provides a composition for increasing sperm survival which consists of proportions of phospholipids and fatty acid chains selected based on differences in membrane lipids caused by cryopreservation. The invention also includes a method for determining the proportions of phospholipids and fatty acid chains selected based on differences in membrane lipids caused by cryopreservation. The phospholipids in the composition for preserving sperm are PC, PE, SPH, PS and PI. The composition has fatty acid chain proportions that imitate the fatty acid chain proportions found in fresh boar sperm membrane with adjustments to broaden the distribution of fatty acid chains in PC, increase the proportion of 18:0 or decrease the proportion of longer unsaturated fatty acids or unsaturated fatty acids. As a result of this invention, damage to sperm during cooling is prevented and reversed. According to the invention, the composition is delivered to boar sperm by a small unilamellar vesicle (SWV). The invention also includes the composition described above, mixed with an extender. The composition of the invention increases sperm survival during cooling, freezing and post-thaw. As a result of this invention, sperm can now be cryopreserved, thawed and used for effective artificial insemination.

The methods and compositions of this invention may also be used to increase survival of the sperm of other species after chilling. The techniques described in this application may be used effectively and modifications can be easily be made by one skilled in the art. Damage to sperm membrane during freezing and thawing is assessed and compositions and methods of this invention prevent and repair the damage. Sperm of other species may also be cryopreserved, thawed and used for artificial insemination in a manner similar to boar sperm.

The invention established compositions and a method to fuse liposomes and boar sperm, and has evaluated the effect of different lipids on porcine sperm during cryopreservation. These compositions and methods can be used to increase viability of other types of sperm after cooling. There are many factors which have been shown to influence fusion and fusion efficiency, which include charge of the lipids, temperature, pH, and presence of fusogenic substances (Huang, 1983). The invention shows that lipids can be successfully incorporated into boar sperm by fusion at 35° C., using the physiological buffer BTS (pH 7.3), thus meeting the basic requirements for maintaining sperm viability. Calcium was not necessary to induce fusion of liposomes to boar sperm. Select lipids consisted of specified proportions of PC, PE, SPH, PS, and PI. Each of these phospholipids contained specified varieties of fatty acid chains. According to previous work (Buhr et al., 1994), these extracted lipids consist of cholesterol, PC, PE, PI, SPH and PS, and each lipid type also has various fatty acyl chains. SUVs are recommended as a convenient liposome tool to fuse with cells (Huang, 1983; Jones and Chapman, 1995). Because of their small diameter and more homogeneous size, SUVs can approach cell membranes more closely (Huang, 1983) and are more easily quantified.

The % sperm with lipids (%SWIL) values were consistently higher in $10^7$ sperm/ml than in $10^8$ sperm/ml with either lipid type. At the end of the incubation, about 60% of sperm at $10^7$ sperm/ml had incorporated SUVs compared to about 40% for $10^8$ sperm/ml. The results showed that incorporation was even higher with $10^6$ sperm/ml than with $10^7$ sperm/ml. With the same concentration of lipids, therefore, the more fusion products can be obtained by using the lower sperm concentration. It is reasonable that, at a given lipid concentration and incubation time, the lower number of sperm have more opportunities to meet and fuse with SUVs, so that the value of % SWIL is higher with the lower concentration of sperm.

Generally the % SWIL values are higher than a previous report (Streiner and Graham, 1993) that only had 2% for live sperm and 18% for dead sperm by using PS/cholesterol liposome to fuse to bull sperm. The interaction between exogenous lipids and sperm membranes is affected by the lipid composition of liposome. Arienti (1997) reported that the liposomes made with lipids extracted from rat liver had much higher fusion efficiency with human sperm than the liposomes made with lipids extracted from the human postasome, which the authors suggested was related to the different composition and/or vesicle size.

According to the present invention the % of available lipids which fused to sperm (%ALFs) was higher for $10^8$ sperm/ml than $10^7$ sperm/ml at all times for SL and at 1 and 10 minutes for HPM lipids. After 10 minutes of incubation, the % ALFS for $10^8$ sperm/ml was similar for SL and HPM. For the $10^7$/ml concentration, the values for SL and HPM were the same at 1 minute of incubation, but as the incubation time increases, sperm took up more HPM lipids than SL lipids. This difference presumably reflects the different compositions and different origin of these two lipids. HPM lipids are extracted from the head plasma membrane, so the lipid composition and structure are the same or similar to those of the boar sperm to which they fuse. The SL lipids are customised lipid products, and thus they are more foreign to the sperm membrane. PS, PI and PE exist as anions or zwitterions at the working pH (Kotyk, 1988), which can improve fusion (Deamer and Uster, 1985). PE is relatively less stable than others. Especially when it contains long fatty acyl chains, PE readily changes its configuration from bilayer phase to $H_{II}$. $H_{II}$ is an inversed micelle, which usually is the immediate structure of fusion between two membranes (Verklei and De Gier, 1981). Some types of PE, such as dioleyl-PE, have been determined as fusogenic factors (Kirjavainen et al, 1996) and have been used as 'helper' lipids to mediate gene transfer (Hui et al., 1996). Inclusion in the liposome membranes of a fusogenic lipid (eg, lysoPC or DOPE) is generally believed to increase the fusion efficiency, while little or no fusion activity was found for liposomes containing PC alone (Huang, 1983). Therefore, it is not surprising that chemical nature of the lipids affected the efficiency with which they fuse to sperm. As the HPM lipids contained lysoPC and more PE with long and unsaturated fatty acid chain (Buhr et al., 1994), HPM liposomes were easer to fuse to sperm than SL liposomes. Subsequent experiments used $10^7$ sperm/ml to maximise the % SWIL, even though this reduced the % ALFS.

The method of the present invention shows that lipids protected sperm viability in the process of slow cooling (0.1 C./min) from 34° C. to 5° C. At the end of cooling, SL either exceeds or equals HPM's protective capability. This phenomenon suggests that the protective effect of lipid is during the cooling stage, contributed mainly by increasing the total amount of lipid and also by adding more of some kinds of lipids which are insufficient in fresh sperm. Parks and Lynch (1992) reported that the ratio of sperm membrane proteins to phospholipids was highest for boar (1.26) compared to other species, such as rooster (0.46), bull (0.8) and stallion (0.86). During the cooling process, some lipids are released from the plasma membrane of boar sperm (reviewed by Bwanga, 1991), and the lower the temperature the greater the proportion of lipids which have undergone a phase transition (Watson 1981; Watson and Plummer, 1985). Both processes disturb the fluidity of the sperm membrane. After taking up lipids, sperm membranes have a greater absolute amount of lipids and a lower ratio of protein to lipids. The greater amount of lipids can compensate for some released lipids and the functions and movements of proteins can be carried out more normally. As the temperature goes down, these exogenous lipids along with the sperm membrane lipids will take part in the activity of stabilising the membrane fluidity. Presumably, the integrity of membrane function can be kept better than in sperm with no additional lipids.

Although the final viability was similar for sperm treated with SL and HPM, their patterns of changing viability differed during the cooling process. This suggests that these two types of lipids have different impacts on boar sperm. Evidently, boar sperm plasma membranes underwent an initial unstable stage while incorporating SL lipids, so that sperm viability in SL was significantly lower than HPM and BTS buffer control at 34° C. This stage, however, could be considered as a modification of lipid composition in sperm membrane and/or as an adjustment for the membrane composition and structure. Actually, the viability value of SL treatment at 34° C. may not be a true reflection of sperm function. It probably reflects a temporary instability of membrane at this time. For some portion of sperm, this instability could have affected the sperm membrane integrity and this allowed a small amount of propidium iodide, which is supposed to be impermeable to the intact membrane, to penetrate this membrane. Once the membrane adjustment was finished, structural integrity of sperm plasma membrane is re-established and propidium iodide can no longer cross the membrane any more but SYBR-14 can permeate. Viability in SL therefore was recovered.

Egg yolk extenders have phospholipids and other components that affect survival of cryopreservation. The freezing method of Pursel and Johnson (1975) as modified for straw freezing (Pettitt, 1996) was employed, using extenders with or without 20% egg yolk. Semen was incubated with either SUVs (made from SL or HPM) or BTS buffer. With 0.1 C./min cooling rate, samples were slowly cooled from 34° C. to 5° C. for 5 hours with a programmable cooler. Extended semen was then frozen in 0.5 cc straw with a cooling rate of 30° C./min down to −70° C. and then plunged into liquid $N_2$ immediately.

The results confirmed that the lipids either from SL or HPM have beneficial effects on sperm function. As in the cooling experiment, the viability of SL-treated sperm was slightly but significantly lower than the HPM and control group at 34° C. Interestingly, the proportion of sperm with progressive movement was higher with SL treatment than either HPM or BTS control (Table 3). However, this may be due to the fact that the SL reduced the stickiness of sperm head to slides rather than directly affecting motility. This was reflected by the similarity of the total motility among treatments at this stage. At 24° C., the parameters of progressive motility and total motility apparently distinguished the effect of SL and HPM on the function of boar sperm (Table 3). Evidently, SL had a superior effect on motility to that of HPM.

SL protected sperm better from the initial impact of adding extender. Within a short time of adding extenders, viability and total motility of SL-treated sperm were higher in either extender. SL also improved progressive motility in the industry-standard extender (BF5 including egg yolk and OEP). The most dramatic change on sperm function was made by egg yolk and OEP. Either parameter in extender plus egg yolk was significantly higher than the corresponding BF5 excluding egg yolk and OEP. This effect remained to the end of cryopreservation.

OEP is a synthetic surfactant which contains detergent sodium, triethanolamine lauryl sulphate and amide binder. The mechanism of action of OEP in the extender is not clearly understood yet, but it has been suggested that OEP acts on the egg yolk lipids rather than the sperm membranes (Strzezek et al., 1984). Because of its amphipathic properties, OEP may disperse and modify the egg yolk lipids, making them more available to sperm plasma membrane (Bwanga, 1991). Addition of OEP into extender containing egg yolk has been associated with increased post thaw motility and normal acrosomes in many species (boar: Graham et al., 1971; Graham and Crabo, 1972, horse: Martin et al., 1979; bull: Arriola and Foote, 1987) and significantly enhanced fertility capacity of bull ( Pursel et al., 1978; Arriola and Foote, 1987).

The concentration of sperm being frozen also influences the survival of sperm in cryopreservation (Bwanga, 1991). However, to obtain the maximum fusion efficiency, $10^7$ sperm/ml was used for the sperm-SUV reaction mixture in this study, and sperm were further diluted during addition of extender B to $0.5 \times 10^7$ sperm/ml. This concentration is far below the commonly recommended freezing concentration for boar semen, which is $45–100 \times 10^7$ sperm/ml (Bwanga, 1991).

Addition of extenders had no immediate impact on sperm function in treatments containing any form of lipids, but, as expected, decreased viability in the BTS-only treatments. This effect may came from the addition of 3% glycerol. Glycerol is one of the cryoprotectants which greatly extend the tolerance of sperm to freezing (Polge, 1980) by lowering of the salt concentrations and/or increasing the unfrozen water fraction (Mazur et al., 1970; Mazur and Cole, 1985). However, it has been suggested that glycerol has a harmful effect on sperm (Watson, 1995) vary with species, concentrations of glycerol which interact with the cooling rates (Polge, 1980). Fiser and Fairful (1989, 1990) recommended, that the combination of 3% glycerol and 30 C./min which was used.

After thawing, sperm frozen in SL+egg yolk/OEP had higher viability and motility than in HPM+egg yolk/OEP, with the industry-standard BTS+egg yolk/OEP being intermediate. SL also significantly improved post-thaw viability, progressive motility and total motility in the absence of egg yolk, but HPM did not. Clearly, the specific lipids in extender do influence the ability of sperm to survive cryopreservation. The overwhelming effect of egg yolk, however, may be due to any of its components. The significant difference between SL+EY/OEP and SL−EY/OEP could be due to the different amount of lipids in those two groups. The SL concentration (0.3119 umole/ml, about 200 ug/ml) is far less than EY (20% of extender). SL lipids also improved the post-thaw survival in egg yolk extender. Basically, select lipids include most types of phospholipids in extender with the exception of lysoPC which is present in extender in the minor amounts. However, as the SL interacted with sperm membrane by prepared small unilamellar vesicles, the incorporation efficiency should be higher than lipids in extender. SL also supplied a high proportion of SPH which was negligible in extender (Buhr et al., 1994).

Egg yolk is rich in cholesterol, which is the major source of steroids in sperm membrane (Buhr et al., 1994). The ratio of cholesterol to phospholipid is close to 1 in human and monkey but very low in bull, ram and boar sperm (Holt and North 1985). Human sperm can replenish cholesterol through fusing with prostasomes (Arienti, 1997), a membrane vesicle in seminal plasma, which contains very high cholesterol (Arvidson et al., 1989). These components may provide protective action through reducing the intensity of cellular dehydration (Courtens and Paquignon 1985) or stabilizing the spermatozoa plasma membrane (Watson, 1975; Watson, 1995). However, HPM has cholesterol and SL does not, so the mere presence of cholesterol does not ensure cryoprotection.

The results demonstrated that HPM lipids had some protective effect during the cooling stage, but their effect, overall, was less than that of SL lipids and they had no beneficial effect on post thaw results, even in egg yolk extender. This implies that not all lipids can improve the post thaw. For the purpose of improving the cryopreservation survival of boar sperm, liposomes (SUVs) made from four phospholipids with specific fatty acid chains were used to incorporate into boar sperm to modify the lipid composition of boar sperm. The selection of these lipids was based on the finding of Buhr et al (1994). They found that cryopreservation altered the compositions of phospholipids and fatty acids by reducing the SPH and increasing PC contents in sperm head plasma membrane. Select lipids contained the phospholipids which was identified in fresh boar sperm membrane. The ratio of these lipids were designed as PC:PE:SPH:PS:PI=20.05:26.32:42.11:5.26:5.26. By fusing, relative lipid content should shift to more SPH and less PC. Meanwhile, the ratio of phospholipids to protein would increase and the proportion of PI would decrease in the sperm membrane, which could make the lipid composition of boar sperm membrane more similar to those of the species which have high cold-resistant ability (Parks and Lynch, 1992).

SL demonstrated its protective effect on sperm function in the absence of egg yolk and this effect on viability and total motility was evident throughout cryopreservation. SL may increase membrane stability. In addition, SL has a lower proportion of long unsaturated chains, especially in PE and PS, and these could also contribute to membrane stability.

All publications, patents and patent applications are herein incorporated by reference in their entirety to the same extent as if each individual publication, patent or patent application was specifically and individually indicated to be incorporated by reference in its entirety.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

REFERENCES

Arienti, G., Carlini, E., and Palmerini, C. A. (1997) Fusion of human sperm to prostasomes at acidic pH. J. membr. Biol. 155: 89–94.

Arriola, J. and Foote, R. H. (1987) Glycerolation and thawing effects on bull spermatozoa frozen in detergent-treated egg yolk and whole egg yolk extenders. J. Dairy Sci. 70: 1664–1670.

Arvidson G. Ronquist G. Wikander G. And Ojteg A. C. (1989) Human prostasome membrane exhibit very high cholesterol/phospholipid ratios yielding high molecular ordering. Biochimica et Biophysica Acta 984: 167–173.

Blumenthal, R., Weinstein, J. N., Sharrow, and Henkat P. (1977) Liposome-lymphocyte interaction: saturable sites for transfer and intracellular release of liposome contents. Proc. Natl. Acad. Sci. USA 74: 5603–5607.

Buhr, M. M., Canvin, A. T. and Bailey, J. L. (1989) Effects of semen preservation on boar spermatozoa head membranes. Gamete Res. 23:441–449.

Buhr, M. M., Curtis, E. F. and Kakuda, N. S. (1994) Composition and behaviour of head membrane lipid of fresh and cryopreserved boar sperm. Cryobiol. 31: 224–238.

Butler, W. J., Roberts, T. K. (1975) Effects of some phosphatidyl compounds on boar spermatozoa following cold shock or slow cooling. J. Reprod. Fert. 43: 183–187.

Bwanga, C. O. (1991) Cryopreservation of boar semen 1: A literature review. Acta Vet. Scand. 32:431–453.

Courten J. L. and paquignon M. (1985) Ultrastructure of fresh, frozen and frozen-thawed spermatozoa of the boar. In: *Deep Freezing of Boar Semen* Proc. 1st Int. con. Deep Freeze. Boar Semen. Uppsala. P. 61–87. Eds. L. A. Johnson and K. Larsson. Swedish University of Agricultural Sciences. Uppsala.

Darin-Bennett, A., Poulos A. and White I. G. (1973) The effect of cold shock and freeze-thawing on release of phospholipids by ram, bull and boar spermatozoa. Aust. J. Biol. Sci. 26:1409–1420.

Darin-Bennett, A., Poulos, A. and White, I. G. (1974) The phospholipids and phospholipid-bound fatty acids and aldehydes of dog and fowl spermatozoa. J. Reprod. Fert. 41:471–474.

Darin-Bennett, A., and White, I. G. (1977) Influence of the cholesterol content of mammalian spermatozoa on susceptibility to cold-shock. Cryobiol. 14:466–470.

Deamer, D. W. and Uster, P. (1985) Relation of liposomes to cell membranes. In: *Structure and Properties of Cell Membranes.* Vol.III, P: 104–119. Ed. Gheorghe Benga CRC Press, Inc. Boca Raton, Fla.

De Leeuw, F. E., Chen, H. C., Colenbrander, B. and Verkleij, A. J. (1990) Cold-induced ultrastructural changes in bull and boar sperm plasma membranes. Cryobiol. 27:171–183.

Fiser P. S. and Fairfull R. W. (1989) the effect of glycerol-related osmotic changes on post-thaw motility and acrosomal integrity of ram spermatozoa. Cryobiology 26: 64–69.

Fiser P. S. And Fairfull R. W. (1990). Combined effect of glycerol concentration and cooling velocity on motility and acrosomal integrity of boar spermatozoa frozen in 0.5 mL straws. Mol. Reprod. Dev. 25:123–129.

Flechon, J. E., Harrison, R. A. P, Flechon, B. And Escaig, J. (1986) Membrane fusion events in the $Ca^{++}$/ionophore—induced acrosome reaction of ram spermatozoa. J. Cell Sci. 81: 43–63.

Foulkes, J. K. (1977) Separation of lipoproteins from egg yolk and their effects on the motility and integrity of bovine spermatozoa. J. Reprod. Fert. 49:277–284.

Gebauer, M. R., Pickett, B. W., and Romarek, R. J. (1970) Motility of bovine spermatozoa extended in "defined" diluents. J. Dairy Sci. 53: 817–823.

Graham. F. and Crabo B. G. (1972) Some factors influencing the freezing of boar spermatozoa. Proc. VIIth Int. Congr. Anim. Reprod. & A. I., Munich 2: 1627–1632.

Graham E. F., Rajamnannan A. H. J., Schmehl M. K. L., Maki-laurila M. And Bower R. E. (1971) Preliminary report on procedure and rationale for freezing boar spermatozoa. A. I. Digest. 19: 12–14.

Hall, J. C., Hadley, J., and Doman, T. (1991) Correlation between changes in rat sperm membrane lipids, protein, and the membrane physical state during epididymal maturation. J. Androl. 12:76–87.

Hofino, P. O. and Almlid, T. (1991) Recent developments in freezing of boar semen with special emphasis on cryoprotectants. In: *Boar Semen Preservation II. Proc. 2nd Int. Con. Boar Semen Preserv.* Beltsville. Suppl. 1. Reprod. Domestic. Anim. Vol (s1) P. 111–112. Eds. L. A. Johnson and D. Rath. Paul Parey Scientific Publishers, Berlin and Hamburg.

Holt, W. V. and North, R. D. (1985) Determination of lipid composition and thermal phase transition temperature in an enriched plasma membrane fraction from ram spermatozoa. J. Reprod. Fert.73:285–294.

Huang, C. H. (1969) Studies on phosphatidylcholine vesicles: Formation and physical characteristics. Biochemistry 8: 334–352.

Huang, L.(1983) Liposome-cell Interactions in vitro. In: *Liposomes.* P.87–115 Ed. Marc J. Ostro, Marcel Dekker, Inc. New York and Basel.

Hui S. W., Langner m., Zhao y. L., Ross P., Hurley E. And Chan K.(1996) The role of helper lipids in cationic liposome-mediated gene transfer. J. Biophys. 71: 590–599.

Johnson, L. A. and Larson, K. (1985) Concluding remarks In: *Deep freezing of boar semen.* Proc. 1st Int. Con. Deep Freeze. Boar Semen. Uppsala. P. 113–127. Eds. L. A. Johnson and K. Larsson. Swedish University of Agricultural Sciences, Uppsala.

Jones, M. N and Chapman, D. (1995) The liposomal state In: *Micelles. Monolayers, and Biomembranes.* P. 117–142. Eds. Malcolm N Jones and Dennis Chapman. A John Wiley & Sons, INC.

Kirjavainen m., Urtti A., Jaaskelainen I., Suhonen T. M., Paronen P., Valjakka-Koskela R., kiesvaara j. And Monkkonen J. (1996) Interaction of liposomes with human skin in vitro—the influence of lipid composition and structure. Biochim. Biophys. Acta. 1304: 179–189.

Kok, J. W. and Hoekstra, D. (1992) Fluorescent lipid analogues: Applications in Cell and Membrane Biology. In: *Fluorescent and Luminescent Probes for Biological Activity*. P.100–119, Ed. W. T. Mason, Academic Press Inc., Harcourt Brace & Company, San Diego.

Kotyk, A. (1988) Membrane structure In: *Biophysical chemistry of membrane functions*. P. 41–115 Eds. Kotyk, A., Janacek, J. and Koryta, J. Jone Wiley & Sons, Chichester, Great Britain.{PRIVATE }

Martin, J. C., Klug, E. and Gunzel, A. R. (1979) Centrifugation of stallion semen and its storage in large volume straws. J. Reprod. Fert., Suppl. 27: 47–51.

Mazur, P. And Cole K. W. (1985) Influence of cell concentration on the contribution of unfrozen fraction and salt concentration to the survival of slowly frozen human erythrocytes. Cryobiol. 22: 509–536.

Mazur, P., Leibo, S. P., Farrant, J., Chu, E. H. Y., Hanna, M. J., and Smith. L. H. (1970) Interaction of cooling rate, warming rate and protective additive on the survival of frozen mammalian cells. In: *The Frozen Cells*. P. 69–85. Eds G. E. Wolstenholme and M. O. Conery. CIBA Foundation Symposium, Londan.

Nikolopoulou, M., Soucek, D. A. and Vary, J. C. (1985) Changes in the lipid content of boar sperm plasma membranes during epididymal maturation. Biochim. Biophys. Acta. 815:486–498.

Nikolopoulou, M., Soucek, D. A., and Vary, J. C.(1986) Modulation of the lipid composition of boar sperm plasma membrane during an acrosome reaction in vitro. Arch. Biochem. Biophys. 250:30–37.

Paquignon, M.(1985) Freezing and thawing extenders for boar spermatozoa. In: *Deep Freezing of Boar Semen*. Proc. 1st Int. Con. Deep Freeze. Boar Semen. Uppsala. P. 129–145. Eds. L. A. Johnson and K. Larsson. Swedish University of Agricultural Sciences, Uppsala.

Parks, J. E. and Lynch, D. V. (1992) Lipid composition and thermotropic phase behaviour of boar, bull, stallion, and rooster sperm membranes. Cryobiol. 29: 255–266.

Pettitt M. J. (1996) Membrane reaction agents and cryopreservation of boar spermatozoa Ph. D thesis, University of Guelph.

Polge C. (1980) Freezing of spermatozoa. In: *Low temperature preservation in medicine and biology*. P.45–64. Eds. Ashwoodsmith M J, Farrant J. Pitman Medical, London.

Poulos, A., Darin-Bennett, A. and White, I. G. (1973) The phospholipid-bound fatty acids and aldehydes of mammalian spermatozoa. Comp. Biochem. Physiol. 46B:541–549.

Pringle, M. and Chapman, D. (1981) Biomembrane structure and effects of temperature. In: *Effects of low temperatures on biological membranes*. P.21–37. Eds. G. J. Morris and A. Clarke. Academic Press, London.

Pursel V. G. And Johnson L. A. (1975) Freezing of boar spermatozoa: fertilizing capacity with concentrated semen and a new thawing procedure. J. Anim. Sci. 40: 99–102.

Pursel, V. G., Johnson, L. A., and Schulman, L. L. (1972) Interaction of extender composition and incubation period on cold shock susceptibility of boar spermatozoa. J. Anim. Sci. 35: 580–584.

Pursel, V. G., Johson, L. A., Schulman, L. L. (1973) Effect of dilution, seminal plasma and incubation period on cold shock susceptibility of boar spermatozoa. J Anim. Sci.37:528–531.

Pursel, V. G., Shulman, L. L., and Johnson, L. A. (1978) Effect of orvus ES paste on acrosomal morphology, motility and fertilizing capacity of frozen thawed boar sperm. J. Anim. Sci. 47: 198–202.

Rana. A. P. S., Majumder, G. C., Misra, S., and Ghosh, A. (1991) Lipid changes of goat sperm plasma membrane during epididymal maturation. Biochim. Biophys. Acta 1061: 185–196.

Robertson, L., Bailey, J. L. and Buhr, M. M. (1990) Effects of cold shock and phospholipase $A_2$ on intact boar spermatozoa and sperm head plasma membrane. Mol. Reprod. Dev. 26: 143–149.

Seki, N., Toyama, Y. and Nagano, T. (1992) Changes in the distribution of filipin-sterol complexes in the boar sperm plasma membrane during epididylmal maturation and in the uterus. Anat. Rec. 232:221–230.

Stojanoff, A., Bourne, H., Andrews, A. G. and Hyne, R. V. (1988) Phospholipid composition of isolated guinea pig outer acrosome membrane and plasma membrane during capacitation in vitro. Gamete Res. 21:297–311.

Streiner, C. F. and Graham, J. K. (1987) The mechanism of phosphatidylserine liposome interaction with sperm for cryopreservation. Cryobiol. 24:42–52.

Streiner C. F. And Graham J. K. (1993) The mechnism of phosphatidylserine liposome interaction with sperm for cryopreservation(abstract). Biol. of Repro. 48: 164.

Struck, D. K., Hoekstra, D. and Pagano, R. E.(1981) Use of resonance energy transfer to monitor membrane fusion. Biochemistry 20:40934099.

Strzezek j. Glogowski J, Magierska e, Luberda z. And Jablonowska C. (1984) Some aspects of cryobiochemistry of boar semen. In: Proc. 10th Int. Congr. Anim. Reprod. And A. I. 2: 224–246. Urbana.-Champaign Verkleij, A. J. and De Gier, J. (1981) Freeze fracture studies on aqueous dispersions of membrane lipids. In: *Liposomes: From Physical Structure To Therapeutic Applications*. P83–100. Ed. C. G. Knight Elsevier/North-Holland Biomedical Press. NY.

Watson, P. F. (1975) The interaction of egg yolk and ram spermatozoa studied with fluorescent probe. J. Reprod. Fert. 42: 105–112.

Watson, P. F. (1981) The effects of cold shock on sperm cell membranes. In: *Effects of low temperatures on biological membranes*. P. 189–218. Eds. G. J. Morris and A. Clarke. Academic Press, London.

Watson, P. E. and Morris, G. J. (1981) Cold shock injury in animal cell. In: *Temperature and Animal Cells*. Eds. K. Bowler and B. J. Fuller Symp. Soc. Exp. Biol. 41:311–340.

Watson, P. F. and Plummer, J. M. (1985) The responses of boar sperm membranes to cold shock and cooling. In: *Deep Freezing of Boar Semen. Proc. 1st Int. Con. Deep Freeze. Boar Semen*. Uppsala. P. 113–127. Eds. L. A. Johnson and K. Larsson. Swedish University of Agricultural Sciences, Uppsala.

Watson P. F. (1995) Recent developments and concepts in the cryopreservation of spermatozoa and the assessment of their post-thawing function Reprod. Fertil. Dev. 7: 871–891.

Wilhelm, K. M., Graham, J. K, and Squires, E. L. (1996) Effects of phosphatidylserine and cholesterol liposomes on the viability, motility, and acrosomal integrity of stallion spermatozoa prior to and after cryopreservation. Cryobiology 33: 320–329.

TABLE 1

APPENDIX 1
Composition of Beltsville F5 Extender (fraction A and B).

| Ingredient | Amount |
| --- | --- |
| Glucose (dextrose) anhydrous ($CH_2OH(CHOH)_4CHO$) M.W. 180.16 | 3.2 gm |
| Tris (hydroxymethyl) aminomethane ($C_4H_{11}NO_3$) M.W. 121.14 | 0.2 mg |
| TES-N-Tris (hydroxymethyl) methyl 2 aminoethane sulphonic acid ($C_6H_{15}NO_6S$) M.W. 229.20 | 1.2 mg |
| Egg yolk** | 20.0 ml |
| Orvus ES paste (Procter and Gamble, Cincinnati, OH) | 0.33 ml |
| Glycerol* ($CH_2OHCHOHCH_2OH$) m.w. 92.10 | 2.00 ml |

Dissolve and bring to 100 ml with distilled water. Centrifuged at 12,000 × g, 10 min at 5C. Extender decanted and stored at −20C for no longer than 4 weeks.
*present in only fraction B.
**: Egg should be very fresh; before use cleaned with 100% alcohol; after alcohol evaporates, separate egg yolk from white (albumen) by using clean paper filter.

APPENDIX 2

Impact of $Ca^{++}$, sperm concentration and lipid type on fusion efficiency (% of Sperm which had incorporated lipids) over time measured by flow cytometry. Sperm (n = 3) ± $Ca^{++}$ were added at time 0 and incubated at 35 C. for the indicated time.

| Lipid | $Ca^{++}$ mM | Sperm #/ml | Incubation Time | | | |
| --- | --- | --- | --- | --- | --- | --- |
| | | | 1 | 10 | 30 | 60 |
| HPM | 0 | $10^7$ | 79.40 ± 5.27[a] | 59.81 ± 3.16[b] | 57.17 ± 4.66[b] | 62.54 ± 2.12[b] |
| | | $10^8$ | 41.28 ± 1.16[a] | 40.46 ± 2.40[a] | 38.27 ± 2.47[a] | 39.09 ± 1.55[a] |
| | 1 | $10^7$ | 77.85 ± 4.13a | 55.67 ± 7.27[b] | 49.55 ± 5.29[b] | 52.42 ± 4.65[b] |
| | | $10^8$ | 47.01 ± 3.19[a] | 39.25 ± 4.11[ab] | 36.69 ± 4.64[ab] | 36.51 ± 4.20[b] |
| | Pooled | $10^7$ | 78.62 ± 3.01[a,A*] | 57.74 ± 3.66[b,A] | 53.36 ± 3.59[b,A*] | 57.48 ± 3.22[b,A] |
| | | $10^8$ | 44.15 ± 1.99[a,A*] | 39.86 ± 2.14[ab,B*] | 37.48 ± 2.37[b,B] | 37.80 ± 2.08[b,B] |
| SL | 0 | $10^7$ | 43.28 ± 5.92[a] | 56.75 ± 3.44[a] | 63.90 ± 7.47[a] | 66.54 ± 14.37[a] |
| | | $10^8$ | 29.40 ± 1.23[a] | 32.53 ± 0.85[a] | 33.26 ± 1.03[a] | 35.87 ± 4.33[a] |
| | 1 | $10^7$ | 49.72 ± 5.85[a] | 61.12 ± 5.18[a] | 64.25 ± 3.52[a] | 67.77 ± 9.87[a] |
| | | $10^8$ | 33.66 ± 2.20[a] | 34.95 ± 0.64 | 33.60 ± 1.02[a] | 35.17 ± 4.00[a] |
| | Pooled | $10^7$ | 46.50 ± 3.99[a,A] | 58.93 ± 3.18[ab,A] | 64.08 ± 3.69[b,A] | 67.16 ± 7.80[b,A] |
| | | $10^8$ | 31.53 ± 1.48[a,B] | 33.74 ± 0.72[a,B] | 33.43 ± 0.65[a,B] | 35.52 ± 2.64[a,B] |

[a,b]: Values within a row with no superscripts in common differ (P < 0.05).
[A,B]: Within a lipid, values for different sperm concentrations differ (P < 0.05) at this incubation time (Analysis was conducted after pooling 0 and 1 mM $Ca^{++}$ data).
*: Within a sperm concentration, HPM lipids had a different fusion efficiency than SL at this incubation time (P < 0.05) (Analysis was conducted after pooling 0 and 1 mM $Ca^{++}$ data).

We claim:

1. A composition for increasing sperm survival in vitro comprising a carrier and a mixture of the following phospholipids: phosphatidylcholine, phosphatidylethanolamine, sphingomyelin, phosphatidylserine, and phosphatidylinositol which are present in an amount effective to improve sperm survival during the cooling, freezing, or thawing of said sperm.

2. The composition of claim 1, wherein the composition is absent of cholesterol.

3. The composition of claim 1, wherein the phospholipids are in a ratio where phosphatidylcholine is about 20: phosphatidylethanolamine is about 25: sphingomyelin is about 40: phosphatidylserine is about 5: and phosphatidylinositol is about 5.

4. The composition of claim 1, wherein the phospholipids are in a ratio where phosphatidylcholine is about 20: phosphatidylethanolamine is about 20: sphingomyelin is about 40: phosphatidylserine is about 10: and phosphatidylinositol is about 10.

5. The composition of claim 1, wherein the phospholipids are in a ratio where phosphatidylcholine is about 25: phosphatidylethanolamine is about 20: sphingomyelin is about 40: phosphatidylserine is about 5: and phosphatidylinositol is about 10.

6. The composition of claim 1, wherein the proportion of each phospholipid is expressed as a percentage of the total number of moles present in the composition (mol %), comprising:

a. phosphatidylcholine with specific fatty acid chains about:
    C16:0=7%
    C18:0=3%
    C18:1=5%
    C18:2=4%
    C20:4=0.8%
    C22:6=0.6%
  b. phosphatidylethanolamine with specific fatty acid chains about:
    C16:0=5%
    C18:0=21%
  c. sphingomyelin with specific fatty acid chains about:
    C16:0=16%
    C18:0=25%
    C22:6=5%
  d. phosphatidylserine with specific fatty acid chains about:
    C16:0=0.5%
    C18:0=4%
    C18:2=0.5%
  e. phosphatidylinositol with specific fatty acid chains about:
    C16:0=0.6%
    C18:0=6%
    C18:1=0.2%
    C18:2=0.6%.

7. The composition of claim 1, wherein the phospholipids are in a vesicle.

8. The composition of claim 7, wherein the vesicle is a small unilamellar vesicle (SUV).

9. The composition of claim 1, wherein the composition is combined with an extender.

10. The composition of claim 9, wherein the extender is selected from the group consisting of Beltsville Thawing Solution, Beltsville F5 Extender, egg yolk and Orvus ES paste.

11. The composition of claim 1, wherein the proportions of phospholipids are selected based on changes in the sperm membrane phospholipid proportions caused by cryopreservation.

12. The composition of claim 11, wherein the proportion of fatty acid chains are adjusted to increase the proportion of 18:0.

13. The composition of claim 1, wherein the sperm is mammalian sperm.

14. The composition of claim 2, wherein the sperm is mammalian sperm.

15. The composition of claim 14, wherein the sperm is selected from the group consisting of boar sperm and bull sperm.

16. The composition of claim 1, wherein the composition increases sperm survival during cooling, freezing and post-thaw.

17. Sperm preserved with the composition of claim 1.

18. Sperm preserved with the composition of claim 2.

19. A method for increasing sperm survival in vitro comprising the step of administering to sperm a composition according to claim 1.

20. The method of claim 19, wherein said composition is administered in a vesicle.

21. The method of claim 20, wherein the vesicle is a small unilamellar vesicle (SUV).

22. A method for increasing sperm survival comprising administering the composition of claim 1.

23. The method of claim 22, wherein the composition is administered in a vesicle.

24. The method of claim 23, wherein the vesicle is a small unilamellar vesicle (SUV).

25. A method of performing artificial insemination in a porcine mammal or bovine mammal, comprising administering sperm preserved with the composition of claim 1 to a female mammal of the same species so that the female becomes impregnated with the sperm.

* * * * *